US009435796B2

(12) United States Patent
Carter et al.

(10) Patent No.: US 9,435,796 B2
(45) Date of Patent: *Sep. 6, 2016

(54) CYANINE DYES

(75) Inventors: Tim Carter, Fairfax, CA (US); Mark Reddington, San Francisco, CA (US)

(73) Assignee: BIOSEARCH TECHNOLOGIES, INC., Petaluma, CA (US)

(*) Notice: Subject to any disclaimer, the term of this patent is extended or adjusted under 35 U.S.C. 154(b) by 120 days.

This patent is subject to a terminal disclaimer.

(21) Appl. No.: 13/179,345

(22) Filed: Jul. 8, 2011

(65) Prior Publication Data

US 2012/0115133 A1  May 10, 2012

Related U.S. Application Data

(60) Division of application No. 12/652,625, filed on Jan. 5, 2010, now Pat. No. 8,436,153, which is a continuation of application No. 11/051,666, filed on Feb. 4, 2005, now Pat. No. 7,705,150.

(60) Provisional application No. 60/542,137, filed on Feb. 4, 2004.

(51) Int. Cl.
| C12Q 1/68 | (2006.01) |
| G01N 33/542 | (2006.01) |
| C12Q 1/37 | (2006.01) |

(52) U.S. Cl.
CPC .............. *G01N 33/542* (2013.01); *C12Q 1/37* (2013.01); *C12Q 2337/00* (2013.01); *G01N 2333/95* (2013.01)

(58) Field of Classification Search
None
See application file for complete search history.

(56) References Cited

U.S. PATENT DOCUMENTS

| 3,649,266 A | 3/1972 | Chapman et al. |
| 5,106,990 A | 4/1992 | Ohno et al. |
| 5,321,130 A | 6/1994 | Yue et al. |
| 5,627,027 A | 5/1997 | Waggoner |
| 5,808,044 A | 9/1998 | Brush et al. |
| 5,968,479 A | 10/1999 | Ito et al. |
| 5,986,086 A | 11/1999 | Brush et al. |
| 5,989,823 A | 11/1999 | Jayasena et al. |
| 6,114,350 A | 9/2000 | Randall et al. |
| 6,140,494 A | 10/2000 | Hamilton et al. |
| 6,197,956 B1 | 3/2001 | Randall et al. |
| 6,224,644 B1 | 5/2001 | Randall et al. |
| 6,294,667 B1 | 9/2001 | Jackson et al. |
| 6,331,632 B1 | 12/2001 | Reedy et al. |
| 6,437,141 B2 | 8/2002 | Randall et al. |
| 6,740,755 B2 | 5/2004 | Caputo et al. |
| 6,747,139 B1 | 6/2004 | Rapoport et al. |
| 6,825,195 B2 | 11/2004 | Kimura |
| 7,230,117 B2 | 6/2007 | Michael et al. |
| 7,868,157 B2 | 1/2011 | Reddington |
| 2004/0146895 A1* | 7/2004 | Cook et al. .................. 435/6 |
| 2007/0021621 A1 | 1/2007 | Reddington |
| 2008/0039415 A1 | 2/2008 | Stewart et al. |

FOREIGN PATENT DOCUMENTS

| JP | 01-233439 | 9/1989 |
| JP | 08-198873 | 8/1996 |
| JP | 09-124599 | 5/1997 |
| WO | WO 97/45539 | 12/1997 |
| WO | WO 01/57526 | 8/2001 |
| WO | WO 02/12398 | 2/2002 |

OTHER PUBLICATIONS

Grant & Hackh's Chemical Dictionary (5th Ed. 1987) at p. 148.*
Heid et al., "Real Time Quantitative PCR," *Genome Research*, 1996, pp. 986-990, vol. 6, Cold Spring Harbor Laboratory Press.
Higuchi et al., "Simultaneous Amplification and Detection of Specific DNA Sequences," *Biotechnology*, Apr. 1993, pp. 413-417, vol. 10.
Holland et al., "Detection of specific polymerase chain reaction product by utilizing the 5'→3' exonuclease activity of *Thermus aquaticus* DNA polymerase," *Proc. Natl. Acad, Sci. USA*, Aug. 1991, pp. 7276-7280, vol. 88.
Lee et al., "Allelic discrimination by nick-translation PCR with fluorogenic probes," *Nucleic Acids Research*, 1993, pp. 3761-3766, vol. 21, No. 16, Oxford University Press.
Mujumdar et al., "Cyanine Dye Labeling Reagents: Sulfoindocyanine Succinimidyl Esters," *Bioconjugate Chem.*, Mar./Apr. 1993, pp. 105-111, vol. 4, No. 2, American Chemical Society.
Nazarenko et al., "A Closed Tube Format for Amplification and Detection of DNA Based on Energy Transfer," *Nucleic Acids Research*, 1997, pp. 2516-2521, vol. 25, No. 12, Oxford University Press.
Sinha et al., "The preparation and application of functionalised synthetic oligonucleotides: III. Use of H-phosphonate derivatives of protected amino-hexanol and mercapto-propanol or -hexanol," *Nucleic Acids Research*, 1988, pp. 2659-2669, vol. 16, No. 6, IRL Press Limited, Oxford, England.
Tyagi et al., "Molecular Beacons: Probes that Fluoresce upon Hybridization," *Nature Biotechnology*, Mar. 1996, pp. 303-308, vol. 14.
Whitcombe et al., "Detection of PCR products using self-probing amplicons and fluorescence," *Nature Biotechnology*, Aug. 1999, pp. 804-807, vol. 17.
Wittwer et al., "Continuous Fluoresence Monitoring of Rapid Cycle DNA Amplification," *BioTechniques*, Jan. 1997, pp. 130-138, vol. 22, No. 1.
Froehler et al., "Nucleoside H-Phosphonates: Valuable Intermediates in the Synthesis of Deoxyoligonucleotides," *Tetrahedron Letters*, 1986, pp. 469-472, vol. 27, No. 4, Pergamon Press Ltd.

* cited by examiner

*Primary Examiner* — Michael Barker
*Assistant Examiner* — Po-Chih Chen
(74) *Attorney, Agent, or Firm* — Morgan, Lewis & Bockius LLP; Jeffry S. Mann

(57) ABSTRACT

The invention provides a novel class of cyanine dyes that are functionalized with a linker moiety that facilitates their conjugation to other species. Also provided are conjugates of the dyes, methods of using the dyes and their conjugates and kits including the dyes and their conjugates.

58 Claims, 4 Drawing Sheets

CYANINE DYES

CROSS-REFERENCE TO RELATED APPLICATIONS

Claim of Priority

This application is a continuation of U.S. patent application Ser. No. 12/652,625, filed Jan. 5, 2010, now U.S. Pat. No. 8,436,153, which is a continuation of U.S. patent application Ser. No. 11/051,666 filed Feb. 4, 2005, now U.S. Pat. No. 7,705,150, and claims priority under 35 U.S.C. §119(e) to U.S. provisional application No. 60/542,137, filed Feb. 4, 2004, the specifications of which are incorporated herein by reference in their entirety for all purposes.

BACKGROUND OF THE INVENTION

1. Field of Invention

The present invention relates generally to the synthesis of fluorescent compounds that are analogues of cyanine dyes. The compounds of the invention are fluorophores that are derivatized to allow their facile attachment to a carrier molecule.

2. Background

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, saccharides, pharmaceuticals, metabolites, microorganisms and other materials of diagnostic value. Examples of such materials include narcotics and poisons, drugs administered for therapeutic purposes, hormones, pathogenic microorganisms and viruses, peptides, e.g., antibodies and enzymes, and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials. The label should give a highly characteristic signal, and should be rarely, and preferably never, found in nature. The label should be stable and detectable in aqueous systems over periods of time ranging up to months. Detection of the label is preferably rapid, sensitive, and reproducible without the need for expensive, specialized facilities or the need for special precautions to protect personnel. Quantification of the label is preferably relatively independent of variables such as temperature and the composition of the mixture to be assayed.

A wide variety of labels have been developed, each with particular advantages and disadvantages. For example, radioactive labels are quite versatile, and can be detected at very low concentrations. However, such labels are expensive, hazardous, and their use requires sophisticated equipment and trained personnel. Thus, there is wide interest in non-radioactive labels, particularly in labels that are observable by spectrophotometric, spin resonance, and luminescence techniques, and reactive materials, such as enzymes that produce such molecules.

Labels that are detectable using fluorescence spectroscopy are of particular interest because of the large number of such labels that are known in the art. Moreover, as discussed below, the literature is replete with syntheses of fluorescent labels that are derivatized to allow their attachment to other molecules, and many such fluorescent labels are commercially available.

In addition to being directly detected, many fluorescent labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, as well as other interactions. An excellent example of the use of fluorescent reporter quencher pairs is found in the detection and analysis of nucleic acids.

Fluorescent nucleic acid probes are important tools for genetic analysis, in both genomic research and development, and in clinical medicine. As information from the Human Genome Project accumulates, the level of genetic interrogation mediated by fluorescent probes will expand enormously. One particularly useful class of fluorescent probes includes self-quenching probes, also known as fluorescence energy transfer probes, or FET probes. The design of different probes using this motif may vary in detail. In an exemplary FET probe, both a fluorophore and a quencher are tethered to a nucleic acid. The probe is configured such that the fluorophore is proximate to the quencher and the probe produces a signal only as a result of its hybridization to an intended target. Despite the limited availability of FET probes, techniques incorporating their use are rapidly displacing alternative methods.

Probes containing a fluorophore-quencher pair have been developed for nucleic acid hybridization assays where the probe forms a hairpin structure, i.e., where the probe hybridizes to itself to form a loop such that the quencher molecule is brought into proximity with the reporter molecule in the absence of a complementary nucleic acid sequence to prevent the formation of the hairpin structure (see, for example, WO 90/03446; European Patent Application No. 0 601 889 A2). When a complementary target sequence is present, hybridization of the probe to the complementary target sequence disrupts the hairpin structure and causes the probe to adopt a conformation where the quencher molecule is no longer close enough to the reporter molecule to quench the reporter molecule. As a result, the probes provide an increased fluorescence signal when hybridized to a target sequence compared to when they are unhybridized Assays have also been developed for detecting a selected nucleic acid sequence and for identifying the presence of a hairpin structure using two separate probes, one containing a reporter molecule and the other a quencher molecule (see, Meringue, et al., *Nucleic Acids Research*, 22: 920-928 (1994)). In these assays, the fluorescence signal of the reporter molecule decreases when hybridized to the target sequence due to the quencher molecule being brought into proximity with the reporter molecule.

One particularly important application for probes that include a reporter-quencher molecule pair is in nucleic acid amplification reactions, such as polymerase chain reactions (PCR), to detect the presence and amplification of a target nucleic acid sequence. In general, nucleic acid amplification techniques have opened broad new approaches to genetic testing and DNA analysis (see, for example, Arnheim et al. *Ann. Rev. Biochem.*, 61: 131-156 (1992)). PCR, in particular, has become a research tool of major importance with applications in, for example, cloning, analysis of genetic expression, DNA sequencing, genetic mapping and drug discovery (see, Arnheim et al., supra; Gilliland et al., *Proc. Natl. Acad. Sci. USA*, 87: 2725-2729 (1990); Bevan et al., *PCR Methods and Applications*, 1: 222-228 (1992); Green et al., *PCR Methods and Applications*, 1: 77-90 (1991); Blackwell et al., *Science*, 250: 1104-1110 (1990)).

Commonly used methods for detecting nucleic acid amplification products require that the amplified product be separated from unreacted primers. This is typically achieved either through the use of gel electrophoresis, which separates the amplification product from the primers on the basis of a size differential, or through the immobilization of the product, allowing free primer to be washed away. However, a number of methods for monitoring the amplification process without prior separation of primer have been described; all of them are based on FET and none of them detect the amplified product directly. Instead, the methods detect some event related to amplification. For that reason, they are accompanied by problems of high background, and are not quantitative, as discussed below.

One method, described in Wang et al. (U.S. Pat. No. 5,348,853; and *Anal. Chem.*, 67: 1197-1203 (1995)), uses an energy transfer system in which energy transfer occurs between two fluorophores on the probe. In this method, detection of the amplified molecule takes place in the amplification reaction vessel, without the need for a separation step.

A second method for detecting an amplification product without prior separation of primer and product is the 5'-nuclease PCR assay (also referred to as the TaqMan™ assay) (Holland et al., *Proc. Natl. Acad. Sci. USA*, 88: 7276-7280 (1991); Lee et al., *Nucleic Acids Res.*, 21: 3761-3766 (1993)). This assay detects the accumulation of a specific PCR product by hybridization and cleavage of a doubly labeled fluorogenic probe (the "TaqMan" probe) during the amplification reaction. The fluorogenic probe consists of a nucleic acid labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Yet another method of detecting amplification products that relies on the use of energy transfer is the "beacon probe" method described by Tyagi et al. (*Nature Biotech.*, 14: 303-309 (1996)) which is also the subject of U.S. Pat. No. 5,312,728 to Lizardi et al. This method employs nucleic acid hybridization probes that can form hairpin structures. On one end of the hybridization probe (either the 5'- or 3'-end) there is a donor fluorophore, and on the other end, an acceptor moiety. In this method, the acceptor moiety is a quencher, absorbing energy from the donor. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus can be used as a measure of the progress of the PCR.

The probes discussed above are most generally configured such that the quencher and fluorophore are on the 3'- and 5'-ends of the probe (Lyamichev et al., *Science*, 260:778-783 (1993)). This spacing of the fluorophore and quencher may impede fluorescent energy transfer: fluorescence energy transfer decreases as the inverse sixth power of the distance between the fluorophore and quencher. Thus, if the quencher is not close enough to the reporter to achieve efficient quenching the background emissions from the probe can be quite high.

To enable the coupling of a fluorescent label with a group of complementary reactivity on a carrier molecule, a reactive derivative of the fluorophore is prepared. For example, Reedy et al. (U.S. Pat. No. 6,331,632) describe cyanine dyes that are functionalized at an endocyclic nitrogen of a heteroaryl moiety with hydrocarbon linker terminating in a hydroxyl moiety. The hydroxyl moiety is converted to the corresponding phosphoramidite, providing a reagent for conjugating the cyanine dye to a nucleic acid. Waggoner (U.S. Pat. No. 5,627,027) has prepared derivatives of cyanine and related dyes that include a reactive functional group through which the dye is conjugated to another species. The compounds set forth in Ohno et al. (U.S. Pat. No. 5,106,990) include cyanine dyes that have a $C_1$-$C_5$ hydrocarbyl linker terminated with a sulfonic acid, a carboxyl or a hydroxyl group. Randall et al. (U.S. Pat. Nos. 6,197,956; 6,114,350; 6,224,644; and 6,437,141) disclose cyanine dyes with a linker arm appended to an endocyclic heteroaryl nitrogen atom. The linkers include a thiol, amine or hydroxyl group, or a protected analogue of these residues. Additional linker arm-cyanine dyes are disclosed by Brush et al. (U.S. Pat. Nos. 5,808,044; 5,986,086). These cyanine dyes are derivatized at both endocyclic heteroaryl nitrogen atoms with a hydrocarbyl linker terminating in a hydroxyl moiety. One hydroxyl moiety is converted to the corresponding phosphoramidite and the other is protected as a dimethoxytrityl ether.

None of the above-described references discloses or suggests modifying the fluorophore nucleus with a versatile amide-linked moiety that allows for the facile variation of the composition, length and degree of branching of the linker. Furthermore, none of the references suggests a linker that provides a locus for attaching the fluorophore to a solid support. Nor do the references describe a branched linker moiety that tethers both a phosphoramidite and dimethoxytrityl ether to a single endocyclic nitrogen atom.

Attaching quenchers or fluorophores to sites other than the readily accessible 5'-OH group generally requires the synthesis of fluorescent labels that attach the fluorophore to a single reactive residue of a carrier molecule or a selected reactive functional group on that residue; reacting the same fluorophore with a different functional group of the carrier generally requires a new modification of the fluorescent core. Similarly, modifying the structure or composition of the linker arm requires a modification to the fluorophore nucleus. Thus, a cyanine label that provides a versatile entry point for an array of synthetic modifications would represent a significant advance in the art.

BRIEF SUMMARY OF THE INVENTION

The inventors have prepared a class of cyanine-based fluorophores modified with a versatile linker arm, the structure of which is readily alterable, thereby allowing the conjugation of the label to a variety of positions, through diverse functional groups, on a carrier molecule. The cyanine-based labels are readily attached to a carrier molecule using techniques well known in the art, or modifications of such techniques that are well within the abilities of those of ordinary skill in the art. The versatility of the labels set forth herein provides a marked advantage over currently utilized cyanine labels, probes assembled using those labels and methods relying upon such labels and probes. Moreover, the present invention provides a class of chemically versatile labels in which the fluorophore can be engineered to have a desired light emission profile.

Thus, in a first aspect, the present invention provides a fluorescent compound having the formula:

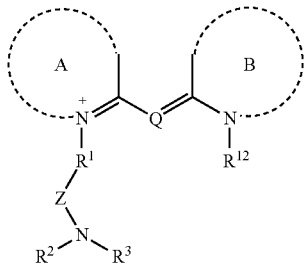

in which A and B are independently selected from substituted or unsubstituted aryl or substituted or unsubstituted heteroaryl moieties. Q is an unsaturated, substituted or unsubstituted, branched-, straight- or cyclic-alkyl or heteroalkyl moiety. Z is $CH_2$ or $C(O)$.

The symbol $R^1$ represents a linker moiety, e.g., a substituted or unsubstituted alkyl, or a substituted or unsubstituted heteroalkyl group. $R^1$ preferably does not comprise a carboxylate group. In another exemplary embodiment, $R^1$ does not include a moiety derived from a carboxylic acid group by replacement of the OH moiety, e.g., an ester, an amide, and an urethane.

In an exemplary embodiment, one or both of $R^2$ and $R^3$ is substituted or unsubstituted alkyl or substituted or unsubstituted heteroalkyl that includes a reactive functional group serving as a locus of attachment between the fluorescent label and a carrier molecule, examples of which include nucleic acids, amino acids, peptides, and saccharides. In another exemplary embodiment, one or both of $R^2$ and $R^3$ are attached to the carrier molecule through a residue derived from the reactive group by its reaction with a complementary group on the carrier molecule. One of $R^2$ and $R^3$ may also be H.

$R^{12}$ is substituted or unsubstituted alkyl, substituted or unsubstituted heteroalkyl, substituted or unsubstituted heterocycloalkyl, substituted or unsubstituted aryl, substituted or unsubstituted heteroaryl and optionally includes a reactive group or a bond to a carrier molecule or solid support.

In a second aspect, the invention provides a fluorescent compound having the formula:

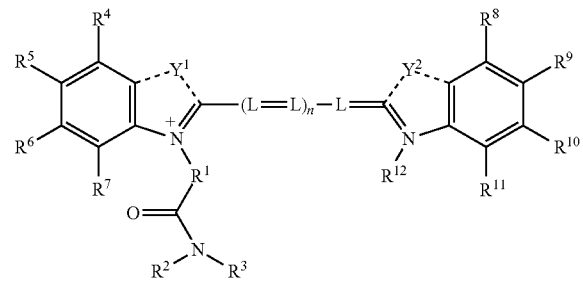

in which $R^4$-$R^{11}$ are generally species independently selected from H and other aryl group substituents as described herein, which optionally include a reactive group. $R^1$ is a linker moiety, e.g., substituted or unsubstituted alkyl, or substituted or unsubstituted heteroalkyl; and $R^{12}$ is substituted or unsubstituted alkyl, substituted or unsubstituted heteroalkyl, substituted or unsubstituted heterocycloalkyl, substituted or unsubstituted aryl, substituted or unsubstituted heteroaryl and optionally includes a reactive group. $Y^1$ and $Y^2$ are members independently selected from $(CR^{y1}R^{y2})_v$ in which each $R^{y1}$ and $R^{y2}$ is independently selected from H and those groups described herein as substituents for alkyl moieties; and each index "v" is independently selected from the integers 1 and 2.

Each L is an independently selected component of an unsaturated, substituted or unsubstituted, straight-, branched-, or cyclic-alkyl or heteroalkyl linker between the two heterocyclic moieties. An exemplary linker component is $C(R^{17})$, in which each $R^{17}$ is independently selected from H, and groups referred to herein as alkyl group substituents (e.g., halide), substituted or unsubstituted alkyl and substituted or unsubstituted heteroalkyl. The $R^{17}$ groups on adjacent linker components can join up together to form a ring. The index "n" is an integer from 0 to 4.

In a third aspect, the invention provides a fluorescent molecule having the formula:

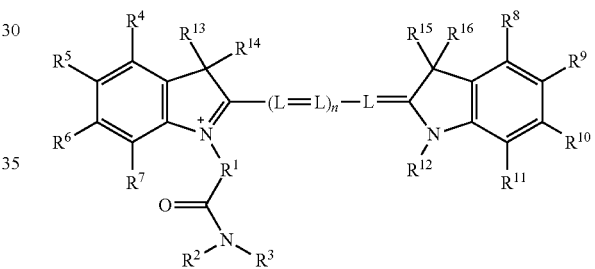

in which the symbol $R^1$ represents substituted or unsubstituted alkyl, and substituted or unsubstituted heteroalkyl groups. $R^1$ preferably does not include a carboxylic acid group. In another exemplary embodiment, $R^1$ does not include a moiety derived from a carboxylic acid group, e.g. an ester, an amide, and an urethane.

$R^2$ is a group such as substituted or unsubstituted alkyl or substituted or unsubstituted heteroalkyl. In an exemplary embodiment, $R^2$ includes a member selected from oxygen-containing reactive functional groups, and carrier molecules, e.g., solid supports.

$R^3$ represents a group such as H, substituted or unsubstituted alkyl, and substituted or unsubstituted heteroalkyl. $R^2$ and $R^3$, together with the nitrogen to which they are attached, are optionally joined to form a ring system. Exemplary ring systems include substituted or unsubstituted $C_5$-$C_7$ cycloalkyl and substituted or unsubstituted 5-7-membered heterocycloalkyl. $R^3$ optionally includes a reactive group.

The symbols $R^4$, $R^5$, $R^6$, $R^7$, $R^8$, $R^9$, $R^{10}$, and $R^{11}$ are each independently selected from groups such as substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN, $Z^1R^{19}$, $NR^{20}R^{21}$, and $C(Z^2)R^{22}$. $Z^1$ is either O or S. $Z^2$ represents O, S or NH. Groups corresponding to $R^{19}$ and $R^{20}$ are independently selected and include H, substituted or unsubstituted alkyl, and substituted or unsubstituted heteroalkyl. $R^{21}$ is selected from H, substituted or unsubstituted alkyl and substituted or unsubstituted heteroalkyl and $C(Z^3)R^{22}$. $R^{20}$ and $R^{21}$, together with the nitrogen to which they are attached, can also be any nitrogen-containing reactive group. Exemplary groups include —NHNH$_2$, —N=C=S and —N=C=O.

$R^{12}$ is substituted or unsubstituted alkyl, substituted or unsubstituted heteroalkyl, substituted or unsubstituted aryl, substituted or unsubstituted heterocycloalkyl, substituted or unsubstituted heteroaryl and optionally includes a reactive group.

$Z^3$ represents O, S or NH. The symbol $R^{22}$ represents groups such as substituted or unsubstituted alkyl, substituted or unsubstituted heteroalkyl, $OR^{23}$, and $NR^{24}R^{25}$. $R^{23}$ represents H, substituted or unsubstituted alkyl, substituted or unsubstituted heteroalkyl, substituted or unsubstituted aryl, substituted or unsubstituted heteroaryl and $C(O)R^{26}$. $R^{24}$ and $R^{25}$ are symbols representing groups independently selected from H, substituted or unsubstituted alkyl and substituted or unsubstituted heteroalkyl. $R^{26}$ is substituted or unsubstituted alkyl or substituted or unsubstituted heteroalkyl.

The symbols $R^{13}$, $R^{14}$, $R^{15}$ and $R^{16}$ represent groups that are independently selected from H, substituted or unsubstituted alkyl and substituted or unsubstituted heteroalkyl.

Each L is as discussed above.

The present invention also provides a conjugate between a carrier molecule, e.g., a nucleic acid, and a fluorescent compound of the invention, which is covalently or ionically bound to a moiety of the carrier molecule. When the carrier molecule is a nucleic acid, representative moieties at which the fluorescent compounds of the invention are attached include the sugar moiety, at both O- and C-centers; endo- and exo-cyclic amines and carbon atoms of nucleobase moieties, and internucleotide bridges. In still a further exemplary embodiment, the conjugate between the compound of the invention and the carrier molecule includes at least one moiety that quenches the fluorescence emission of the compound of the invention.

Other aspects, embodiments and objects of the present invention will be apparent from the detailed description that follows.

DETAILED DESCRIPTION OF THE INVENTION

Abbreviations

Figure 1A:
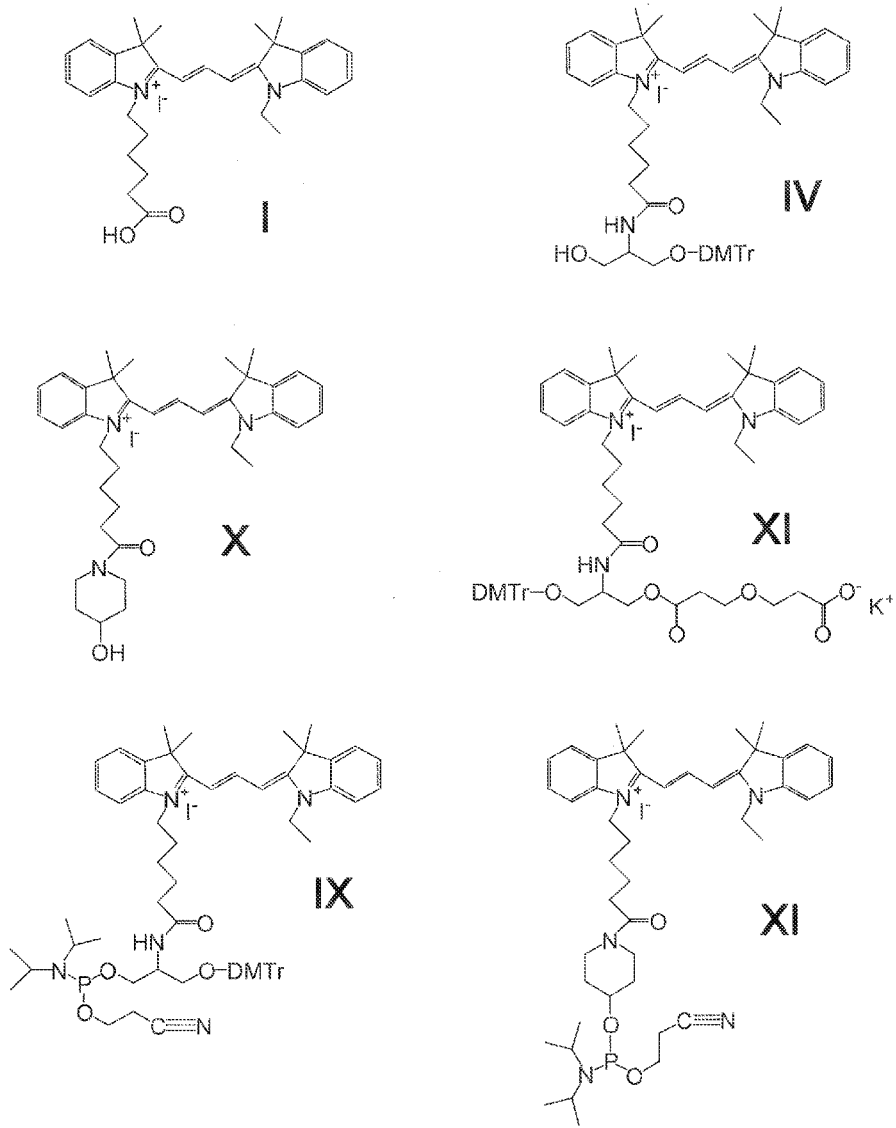
FIGS. 1A, 1B, 1C and 1D display representative compounds of the invention.

"FET," as used herein, refers to "Fluorescence Energy Transfer."

"FRET," as used herein, refers to "Fluorescence Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Definitions

Where chemical moieties are specified by their conventional chemical formulae, written from left to right, they equally encompass the moiety which would result from writing the structure from right to left, e.g., —CH$_2$O— is intended to also recite —OCH$_2$—; —NHS(O)$_2$— is also intended to represent. —S(O)$_2$HN—, etc.

"Cyanine," as used herein, refers to polymethine dyes such as those based upon the cyanine, merocyanine, styryl and oxonol ring.

As used herein, "nucleic acid" means any natural or non-natural nucleoside, or nucleotide and oligomers and polymers thereof, e.g., DNA, RNA, single-stranded, double-stranded, triple-stranded or more highly aggregated hybridization motifs, and any chemical modifications thereof. Modifications include, but are not limited to, conjugation with a compound of the invention or a construct that includes a compound of the invention covalently attached to a linker that tethers the compound to the nucleic acid, and those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids.

Exemplary modified nucleic acids include, but are not limited to, peptide nucleic acids (PNAs), those with phosphodiester group modifications (e.g., replacement of O$^-$ with OR, NR, or SR), 2'-, 3'- and 5'-position sugar modifications, modifications to the base moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of P(O)O$_3$ with another moiety, methylations, unusual base-pairing combinations such as the isobases, isocytidine and isoguanidine and the like. Nucleic acids can also include non-natural bases, e.g., nitroindole. Non-natural bases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

"Nucleic acid" also includes species that are modified at one or more internucleotide bridges (e.g., P(O)O$_3$) by replacing or derivatizing an oxygen of the bridge atom with a compound of the invention or a species that includes a compound of the invention attached to a linker. For example, "nucleic acid" also refers to species in which the P(O)O$_2$ moiety (the O$^-$ moiety remains unchanged or is converted to "OR") of a natural nucleic acid is replaced with a non-natural linker species, e.g., —ORP(O)O—, —ROP(O)R—, —ORP(O)OR—, —ROP(O)OR—, or —RP(O)R— in which the symbol "-" indicates the position of attachment of the linker to the 2'-, 3'- or 5'-carbon of a nucleotide sugar moiety, thus allowing the placement of the exemplified, and other, non-natural linkers between adjacent nucleoside sugar moieties. Exemplary linker subunits ("R") include substituted or unsubstituted alkyl and substituted or unsubstituted heteroalkyl moieties. "R" can include a compound of the invention or a construct of a linker and a compound of the invention.

Furthermore, "nucleic acid" includes those species in which one or more internucleotide bridge does not include phosphorus: the bridge being optionally modified with a compound of the invention or a linker arm-cyanine dye construct. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a compound of the invention or a linker construct that includes a compound of the invention. The discussion above is not limited to moieties that include a carbon atom as the point of attachment; the locus can also be another appropriate linking atom, such as nitrogen or another atom.

Those of skill in the art will understand that in each of the "nucleic acid" compounds described above, the structure corresponding to the term "compound of the invention" can be interchanged with a quencher, a hybridization enhancer, and intercalator, a minor groove binder, a chelating agent, a metal chelate or other moiety that is usefully conjugated to a nucleic acid, optionally being present in tandem with species that include a compound of the invention or a derivative thereof.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Bioactive species," refers to molecules that, when administered to an organism, affect that organism. Exemplary bioactive species include pharmaceuticals, pesticides, herbicides, growth regulators and the like. Bioactive species encompasses small molecules (i.e., approximately <1,000 daltons), oligomers, polymers and the like. Also included are nucleic acids and their analogues, peptides and their analogues and the like.

"Carrier molecule," as used herein refers to any molecule to which a compound of the invention is attached. Representative carrier molecules include a protein (e.g., enzyme, antibody), glycoprotein, peptide, saccharide (e.g., mono-, oligo-, and poly-saccharides), hormone, receptor, antigen, substrate, metabolite, transition state analog, cofactor, inhibitor, drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism.

"Activated derivatives of hydroxyl moieties," and equivalent species, refer to compounds in which an oxygen-containing leaving group is formally accessed through a hydroxyl moiety.

"Activated derivatives of carboxyl moieties," and equivalent species, refer to compounds in which an oxygen-containing leaving group is formally accessed through a carboxyl moiety.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene" and those derivatives of alkyl defined in more detail below, such as "heteroalkyl." Alkyl groups, which are limited to hydrocarbon groups, are termed "homoalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multivalent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups.

When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$ NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

"Analyte", "target", "substance to be assayed", and "target species," as utilized herein refer to the species of interest in an assay mixture. The terms refer to a substance, which is detected qualitatively or quantitatively using a material, process or device of the present invention. Examples of such substances include cells and portions thereof, enzymes, antibodies, antibody fragments and other biomolecules, e.g., antigens, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as α-fetoprotein, carcinoembryonic antigen (CEA), CA 125, CA 19-9 and the like; various proteins, glycoproteins and complex glycolipids such as $\beta_2$-microglobulin ($\beta_2$ m), ferritin and the like; various hormones such as estradiol ($E_2$), estriol ($E_3$), human chorionic gonadotropin (hCG), luteinizing hormone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

The term "drug" or "pharmaceutical agent," refers to bioactive compounds that cause an effect in a biological organism. Drugs used as affinity moieties or targets can be neutral or in their salt forms. Moreover, the compounds can be used in the present method in a prodrug form. Prodrugs are those compounds that readily undergo chemical changes under physiological conditions to provide the compounds of interest in the present invention.

Introduction

The present invention provides a class of reactive fluorescent compounds that are based upon the cyanine nucleus. Also provided is a wide variety of conjugates of the cyanine dyes with carrier molecules, including biological, non-biological and biologically active species. Selected cyanine labels described herein include a functionalized linker arm that is readily converted into an array of reactive derivatives without requiring a modification of the cyanine nucleus. Accordingly, the compounds of the invention provide an, as yet, undisclosed advantage, allowing facile access to an array of conjugates between the linker arm-derivatized cyanine nucleus and carrier molecules.

Residing in the field of fluorescent labels, the present invention provides benefits of particular note. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity and high specificity in labeling. Many fluorescent labels based upon the cyanine-nucleus are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate cyanine-based fluorophore for a particular application and, if it not readily available commercially, will be able to synthesize the necessary fluorophore de novo or synthetically modify commercially available cyanine compounds to arrive at the desired fluorescent label.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

In a first aspect, the present invention provides a fluorescent compound having the formula:

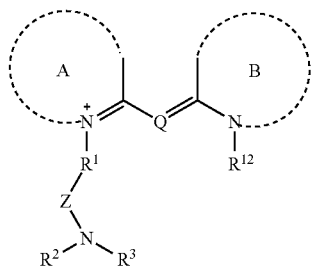

in which A and B are independently selected from substituted or unsubstituted aryl or substituted or unsubstituted heteroaryl moieties. Q is an unsaturated, substituted or unsubstituted, branched-, straight- or cyclic-alkyl or heteroalkyl moiety. Z is $CH_2$ or $C(O)$.

The symbol $R^1$ represents a linker moiety, e.g., a substituted or unsubstituted alkyl, or a substituted or unsubstituted heteroalkyl group. $R^1$ preferably does not comprise a carboxylic acid group. In another exemplary embodiment, $R^1$ does not include a moiety derived from a carboxylic acid group by replacement of the OH moiety, e.g. an ester, an amide, and an urethane.

In an exemplary embodiment, one or both of $R^2$ and $R^3$ is substituted or unsubstituted alkyl or substituted or unsubstituted heteroalkyl that includes a reactive functional group serving as a locus of attachment between the fluorescent label and a carrier molecule, examples of which include nucleic acids, amino acids, peptides, and saccharides. In another exemplary embodiment, one or both of $R^2$ and $R^3$ are attached to the carrier molecule through a residue derived from the reactive group by its reaction with a complementary group on the carrier molecule. One of $R^2$ and $R^3$ may also be H.

In an exemplary embodiment, $R^2$ includes a member selected from oxygen-containing reactive functional groups, solid supports and carrier molecules.

In another exemplary embodiment, $R^2$ and $R^3$, together with the nitrogen to which they are attached, are optionally joined to form a ring system. Exemplary ring systems include substituted or unsubstituted $C_5$-$C_7$ cycloalkyl and substituted or unsubstituted 5-7-membered heterocycloalkyl.

$R^{12}$ is substituted or unsubstituted alkyl, substituted or unsubstituted heteroalkyl, substituted or unsubstituted heterocycloalkyl, substituted or unsubstituted aryl, substituted or unsubstituted heteroaryl and optionally includes a reactive group or a bond to a carrier molecule or solid support.

In a second aspect, the invention provides a fluorescent compound having the formula:

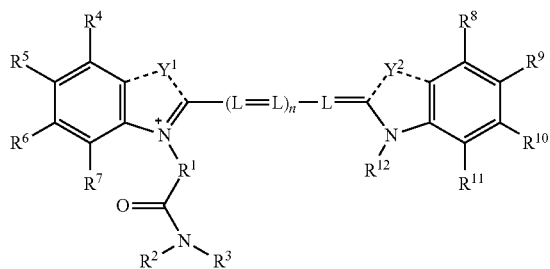

in which $R^4$-$R^{11}$ are generally species independently selected from H and other aryl group substituents as described herein, which optionally include a reactive group. $R^1$ is a linker moiety, e.g., substituted or unsubstituted alkyl, or substituted or unsubstituted heteroalkyl; and $R^{12}$ is substituted or unsubstituted alkyl, substituted or unsubstituted heteroalkyl, substituted or unsubstituted heterocycloalkyl, substituted or unsubstituted aryl, substituted or unsubstituted heteroaryl and optionally includes a reactive group. $Y^1$ and $Y^2$ are members independently selected from $(CR^{y1}R^{y2})_v$ in which each $R^{y1}$ and $R^{y2}$ is independently selected from H and those groups described herein as substituents for alkyl moieties; and each index "v" is independently selected from the integers 1 and 2.

Each L is an independently selected component of an unsaturated, substituted or unsubstituted, straight-, branched-, or cyclic-alkyl or heteroalkyl linker between the two heterocyclic moieties. An exemplary linker component is $C(R^{17})$, in which each $R^{17}$ is independently selected from H, and groups referred to herein as alkyl group substituents (e.g., halide), substituted or unsubstituted alkyl and substituted or unsubstituted heteroalkyl. The $R^{17}$ groups on adjacent linker components can join up together to form a ring. The index "n" is an integer from 0 to 4.

In a third aspect, the invention provides a fluorescent molecule having the formula:

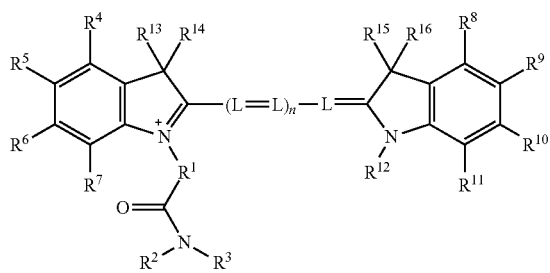

in which the symbol $R^1$ represents substituted or unsubstituted alkyl, and substituted or unsubstituted heteroalkyl groups. $R^1$ preferably does not include a carboxylic acid group. In another exemplary embodiment, $R^1$ does not include a moiety derived from a carboxylic acid group, e.g. an ester, an amide, and an urethane.

$R^2$ is a group such as substituted or unsubstituted alkyl or substituted or unsubstituted heteroalkyl. In an exemplary embodiment, $R^2$ includes a member selected from oxygen-containing reactive functional groups, and carrier molecules, e.g., solid supports.

$R^3$ represents a group such as H, substituted or unsubstituted alkyl, and substituted or unsubstituted heteroalkyl. $R^2$ and $R^3$, together with the nitrogen to which they are attached, are optionally joined to form a ring system. Exemplary ring systems include substituted or unsubstituted $C_5$-$C_7$ cycloalkyl and substituted or unsubstituted 5-7-membered heterocycloalkyl. $R^3$ optionally includes a reactive group.

The symbols $R^4$, $R^5$, $R^6$, $R^7$, $R^8$, $R^9$, $R^{10}$, and $R^{11}$ are each independently selected from groups such as substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN, $Z^1R^{19}$, $NR^{20}R^{21}$, and $C(Z^2)R^{22}$. $Z^1$ is either O or S. $Z^2$ represents O, S or NH. Groups corresponding to $R^{19}$ and $R^{20}$ are independently selected and include H, substituted or unsubstituted alkyl, and substituted or unsubstituted heteroalkyl. $R^{21}$ is selected from H, substituted or unsubstituted alkyl and substituted or unsubstituted heteroalkyl and $C(Z^3)R^{22}$. $R^{20}$ and $R^{21}$, together with the nitrogen to which they are attached, can also be any nitrogen-containing reactive group. Exemplary groups include $-NHNH_2$, $-N=C=S$ and $-N=C=O$.

$R^{12}$ is substituted or unsubstituted alkyl, substituted or unsubstituted heteroalkyl, substituted or unsubstituted aryl, substituted or unsubstituted heterocycloalkyl, substituted or unsubstituted heteroaryl and optionally includes a reactive group.

$Z^3$ represents O, S or NH. The symbol $R^{22}$ represents groups such as substituted or unsubstituted alkyl, substituted or unsubstituted heteroalkyl, $OR^{23}$, and $NR^{24}R^{25}$. $R^{23}$ represents H, substituted or unsubstituted alkyl, substituted or unsubstituted heteroalkyl, $R^{24}$ substituted or unsubstituted aryl, substituted or unsubstituted heteroaryl and $C(O)R^{26}$. $R^{24}$ and $R^{25}$ are symbols representing groups independently selected from H, substituted or unsubstituted alkyl and substituted or unsubstituted heteroalkyl. $R^{26}$ is substituted or unsubstituted alkyl or substituted or unsubstituted heteroalkyl.

The symbols $R^{13}$, $R^{14}$, $R^{15}$ and $R^{16}$ represent groups that are independently selected from H, substituted or unsubstituted alkyl and substituted or unsubstituted heteroalkyl.

Each L is as discussed above.

Representative $-(L=L)_n-L=$ moieties of use in the various aspects of the invention include:

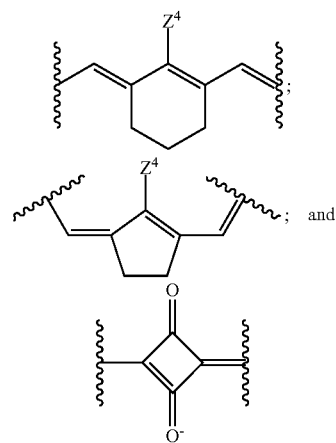

in which $Z^4$ is H, substituted or unsubstituted alkyl, substituted or unsubstituted heteroalkyl, substituted or unsubstituted aryl, substituted or unsubstituted heteroaryl, substituted or unsubstituted heterocycloalkyl or another moiety selected from the substituents for alkyl moieties described herein In a representative embodiment, the invention provides a cyanine dye in which $R^2$ includes a moiety having the formula:

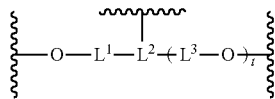

wherein $L^1$, $L^2$ and $L^3$ are members independently selected from substituted or unsubstituted alkyl and substituted or unsubstituted heteroalkyl. The index "t" is 0 or 1.

A subset of $R^2$ moieties according to the motif set forth above have the formula:

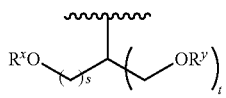

in which the symbols $R^x$ and $R^y$ represent groups that are independently selected from H, substituted or unsubstituted alkyl and substituted or unsubstituted heteroalkyl, a hydroxyl-protecting group, a phosphate moiety, a phosphodiester moiety, a phosphorus-containing internucleotide bridge, a solid support, a carrier molecule and —OP(OR$^o$)(N(R$^p$R$^q$)). The groups represented by the symbols $R^o$, $R^p$ and $R^q$ are members independently selected from H, substituted or unsubstituted $C_1$-$C_6$ alkyl and substituted or unsubstituted $C_1$-$C_6$ heteroalkyl; and the index "s" is an integer from 1 to 20. In an exemplary embodiment, $R^o$ is $CH_2CH_2CN$.

The invention also provides fluorescent compounds in which at least one of $R^x$ and $R^y$ comprises a moiety having the formula:

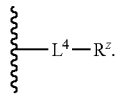

$L^4$ is a member selected from a bond, substituted or unsubstituted alkyl and substituted or unsubstituted heteroalkyl; and $R^z$ is a member selected from a reactive functional group, solid support, a nucleic acid, a saccharide and a peptide. In selected compounds of the invention, $L^4$ comprises a moiety having the formula:

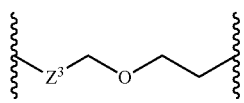

wherein the symbol $Z^3$ represents either $CH_2$ or C=O.

In another embodiment, the invention provides cyanine dyes in which one of the substituents on the cyanine nucleus, preferably $R^{12}$, includes a moiety having the structure:

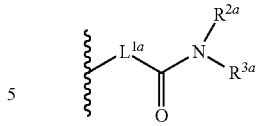

in which $L^{1a}$ is a member selected from substituted or unsubstituted alkyl, and substituted or unsubstituted heteroalkyl groups. The symbols $R^{2a}$ and $R^{3a}$ represent groups that are independently selected from H, substituted or unsubstituted alkyl, and substituted or unsubstituted heteroalkyl. The groups $R^2$ and $R^3$, together with the nitrogen to which they are attached, are optionally joined to form a ring. Preferred ring structures include substituted or unsubstituted $C_5$-$C_7$ cycloalkyl and substituted or unsubstituted 5-7-membered heterocycloalkyl.

An exemplary linker species according to the motif presented above includes an $NR^2R^3$ moiety that has the formula:

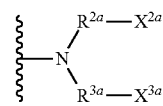

in which $R^{2a}$ and $R^{3a}$ are members independently selected from substituted or unsubstituted alkyl and substituted or unsubstituted heteroalkyl. The symbols $X^{2a}$ and $X^{3a}$ represent groups that are independently selected from H, substituted or unsubstituted lower alkyl, substituted or unsubstituted heteroalkyl, reactive functional groups and a bond to a carrier molecule. When the carrier molecule is a nucleic acid, the bond can be to a nucleobase (e.g., to C or N), sugar (e.g., to C or O) or internucleotide bridge (e.g., to P, O, S, C or N).

Exemplary identities for $X^{2a}$ and $X^{3a}$ include —$CH_3$, —OH, —COOH, —$NH_2$, —SH, and —OP(OX')(N(X")$_2$) in which X' and X" are members independently selected from substituted or unsubstituted alkyl. In an exemplary compound of the invention X' is cyanoethyl; and both X" moieties are isopropyl. When $X^{2a}$ and $X^{3a}$ are components of linkages between a species of the invention and a carrier molecule, the group is modified in a manner that satisfies the rules of valence, e.g., —OH becomes —O—; COOH becomes COOR, CONRR', etc.

In another preferred embodiment, a member selected from $R^{2a}$, $R^{3a}$ and combinations thereof comprises a polyether. Preferred polyethers include, for example, poly (ethylene glycol), poly(propyleneglycol) and copolymers thereof. The polyether may be internal to $R^{2a}$ or $R^{3a}$ group or it may form the free terminus of the group. When the polyether is at the terminus of the group, the terminal —O— moiety is present as —OH, alkoxy or one of a variety of the groups referred to herein as substituents for alkyl moieties. See, for example, Shearwater Polymers, Inc., Catalog: Polyethylene Glycol Derivatives 2002.

In a further exemplary embodiment, $NR^2R^3$ has the formula:

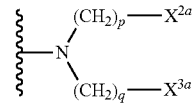

in which the indexes p and q are integers independently selected from 1 to 20, inclusive, preferably from 2 to 16, inclusive.

In yet another exemplary embodiment, $NR^2R^3$ has the formula:

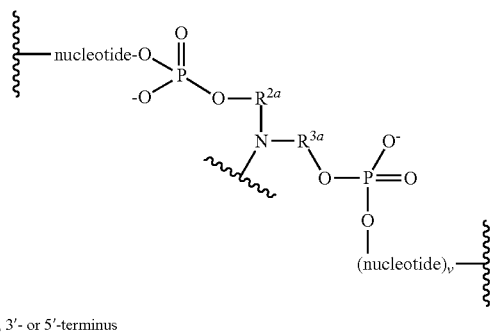

v = 0; 3'- or 5'-terminus in which the index "v" is 0 or 1. $R^{2a}$ and $R^{3a}$ are independently selected substituted or unsubstituted alkyl or substituted or unsubstituted heteroalkyl moieties. When "v" is 0, the phosphate shown can alternatively be OH. Although represented as interposed between two nucleotides, the fluorescent label of the invention can be placed at any point between two nucleoside or nucleotide subunits in a nucleic acid. Thus, exemplary compounds include $NR^2R^3$ at an internal position of the nucleic acid, and tethered to the nucleic acid at the linkage between the 5' and 5'-1 residues and/or the linkage between the 3' and 3'-1 residues In a further exemplary embodiment, $NR^2R^3$ has the formula:

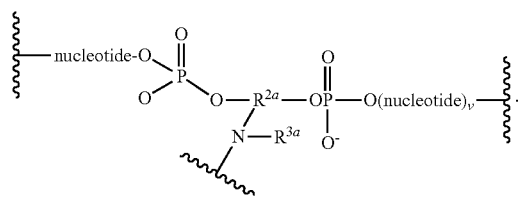

when v = 0; 3'- or 5'-terminus

When "v" is 0, the phosphate group is optionally an OH group.

The invention also provides nucleic acid derivatives in which a compound of the invention is conjugated to a sugar moiety of the nucleic acid. An exemplary species according to this motif has the formula:

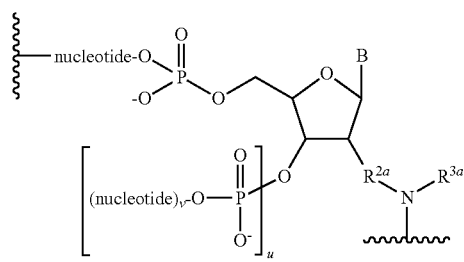

in which the index u represents 0, 1 or a number greater than one. Although shown attached to the 2'carbon of the 3'-terminus of the nucleic acid, those of skill will appreciate that a similar structure tethered to the 5'-terminus, or an internal site of the nucleic acid is within the scope of the invention. Moreover, the group can be tethered through the O atom of a 2'-hydroxyl. When "u" is 0, the phosphate/phosphodiester group is optionally OH.

Moreover, the agents of the invention can be conjugated through the 3'- and/or 5'-hydroxyl moiety of a nucleic acid.

Figure 1B:
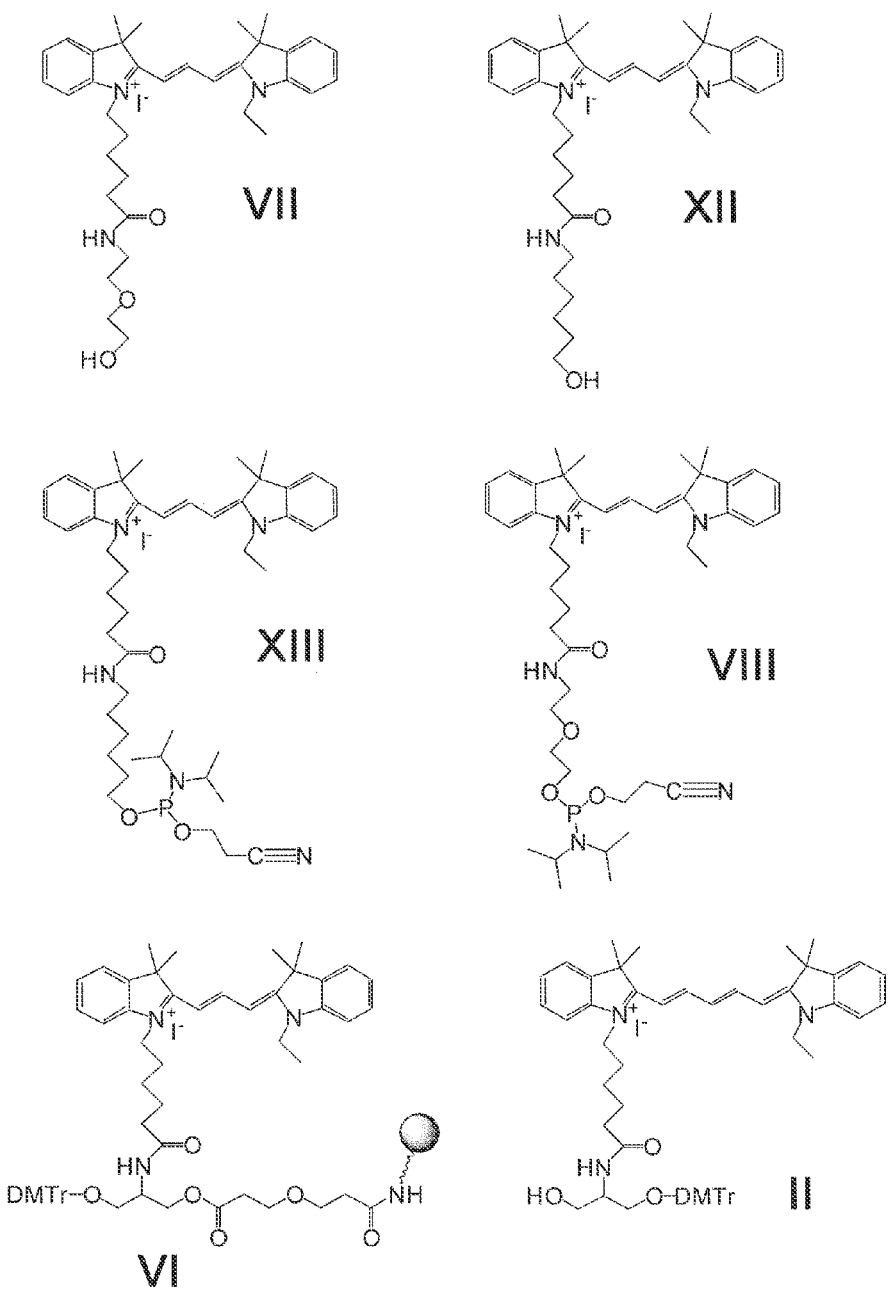
Figure 1C:
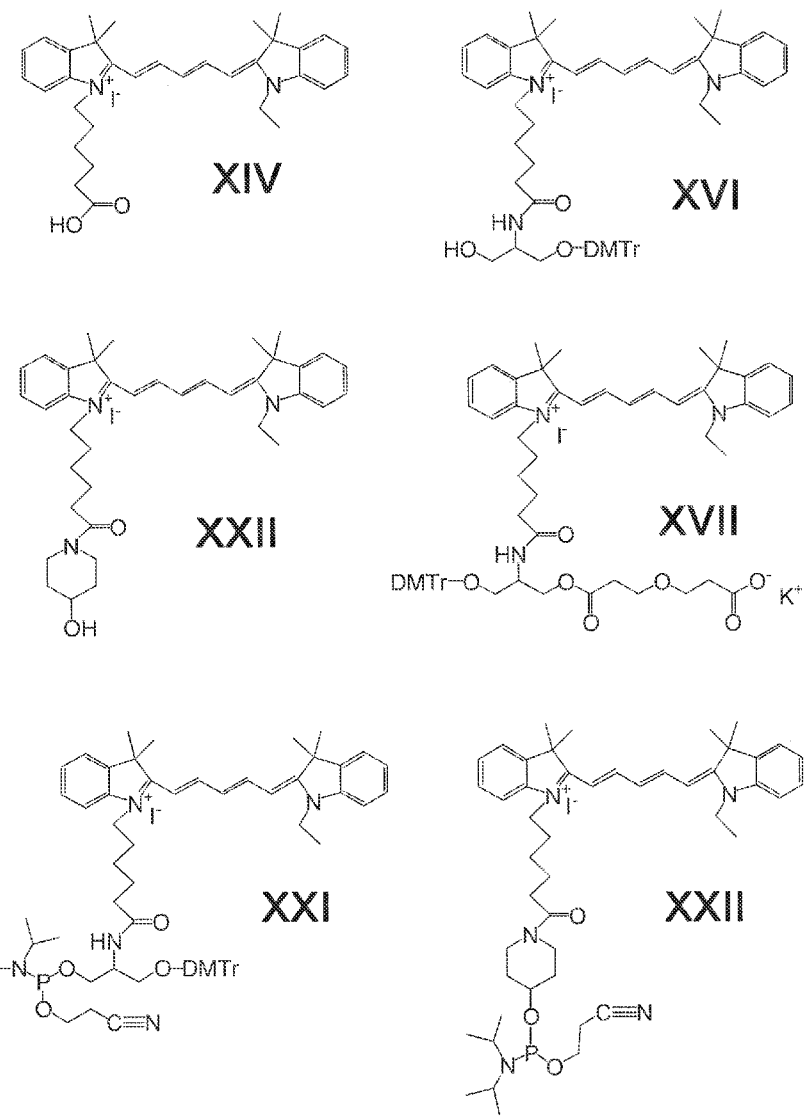
Figure 1D:
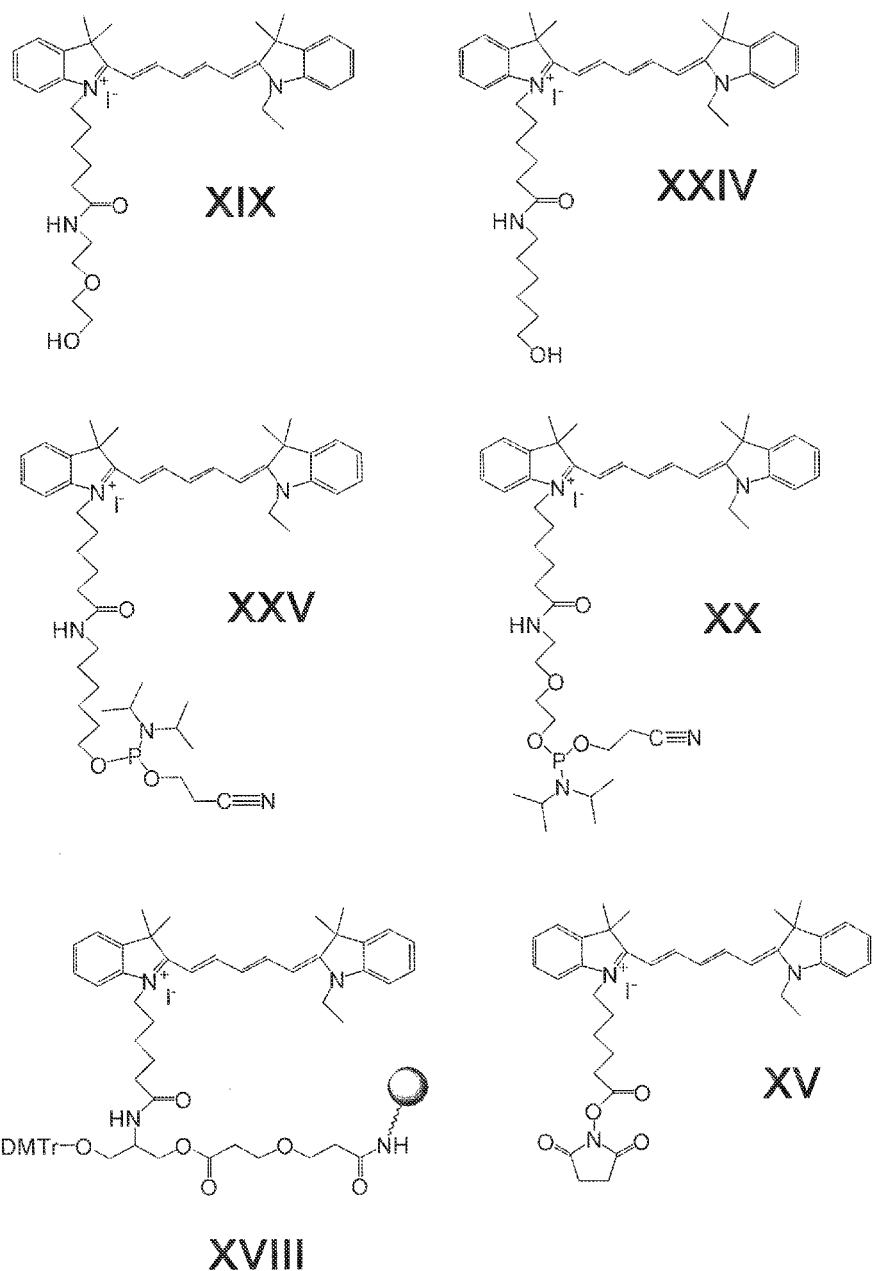

Representative compounds of the invention are set forth in FIG. 1.

In another exemplary embodiment, the invention provides cyanine dyes having a formula selected from:

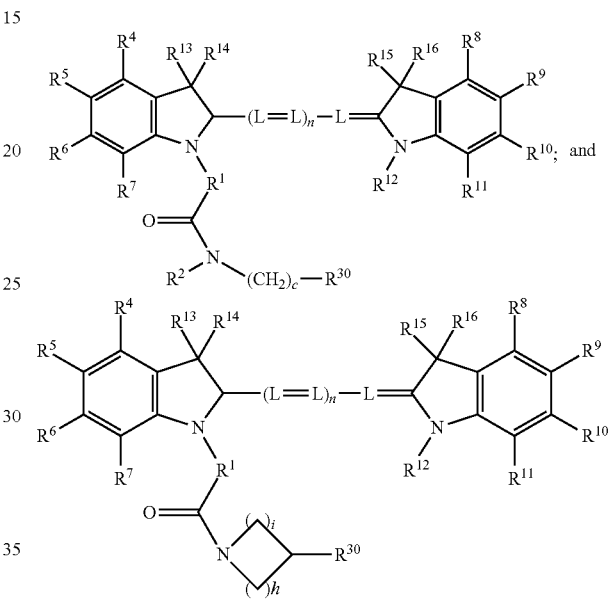

in which the symbol $R^{30}$ represents OH, $OP(OR^o)$ $(NR^pR^q))_2$, $-L^c-R^{31}$ or $R^{35}O(CH_2)_jL^c(R^{31})$, in which $(CH_2)_c$ is attached to $L^c$. $L^c$ is a bond or linker selected from substituted or unsubstituted alkyl and substituted or unsubstituted heteroalkyl bonded to $R^{31}$. $R^{31}$ is OH, $OP(OR^o)(N(R^pR^q))$, a nucleic acid, a phosphoramidite of a nucleic acid, a nucleic acid linked to a solid support, and amino acid, a protected amino acid, an amino acid attached to a solid support, an amino acid residue of a peptide, a carboxylate or an activated carboxylate. The symbols $R^o$, $R^p$ and $R^q$ independently represent H, substituted or unsubstituted $C_1$-$C_6$ alkyl or substituted or unsubstituted $C_1$-$C_6$ heteroalkyl. The index c is an integer from 0 to 20, and the index j is an integer selected from 1 to 20. $R^{35}$ is H or a hydroxyl protecting group (e.g., trityl or substituted trityl). $R^1$-$R^{16}$ are as discussed above.

An exemplary species according to $L^c$ has the formula:

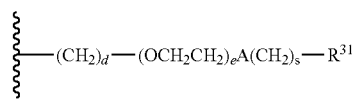

in which the indices d and s are independently selected from the integers from 0 to 10. The index e is an integer from 0 to 1,000. Generally, at least one of d, s and e is at least 1. A is a bond, NH, S or O. The symbol $R^{31}$ is as discussed above.

In another exemplary embodiment, -L$^c$-R$^{31}$ has the formula:

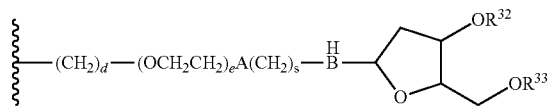

wherein the symbol A represents O, S or NH. B is a nucleic acid base. R$^{32}$ is H, P(OR$^o$)(N(R$^p$R$^q$)) or L$^g$-R$^{34}$. L$^g$ is a bond, an internucleotide phosphodiester bridge, a substituted or unsubstituted alkyl group or a substituted or unsubstituted heteroalkyl moiety. The symbol R$^{34}$ represents OH, a solid support, P(OR$^o$)(N(R$^p$R$^q$)) or a nucleic acid.

R$^{33}$ is a hydroxyl protecting group (e.g., trityl or a substituted trityl, see, for example, Jones, AMINO ACID AND PEPTIDE SYNTHESIS, Oxford Science Publications, Oxford (1992)), OH, a solid support, P(OR$^o$)(N(R$^p$R$^q$)), or a nucleic acid.

An exemplary nucleic acid according to this embodiment has the formula:

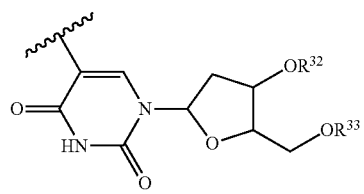

in which R$^{32}$ and R$^{33}$ are as discussed above.

In another embodiment, the cyanine fluorophore is attached to an amino acid, preferably through a linker. For example compounds within the scope of the present invention include those in which R$^{12}$ has the formula:

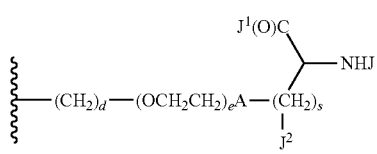

in which J is H or an amine protecting group, generally a protecting group recognized in the peptide synthesis art (e.g., t-Boc, FMOC, etc.; see, for example, Jones, AMINO ACID AND PEPTIDE SYNTHESIS, Oxford Science Publications, Oxford (1992)). J$^1$ is a member selected from H, activating groups and amino acids. J$^2$ is H, substituted or unsubstituted alkyl or substituted or unsubstituted heteroalkyl. A and the indices d, s and e are as discussed above.

In yet a further exemplary embodiment, the invention provides a compound in which R$^{32}$ has the formula:

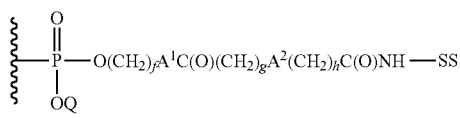

wherein A$^1$ and A$^2$ are independently selected from a bond, O and NH. The symbol SS represents a solid support. Q is a member selected from O$^-$ and substituted or unsubstituted alkyl; and f, g, and h are integers independently selected from 0 to 20. In selected species according to this motif A$^1$ and A$^2$ are both O.

Synthesis

The compounds of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention. It is not intended to define the scope of reactions or reaction sequences that are useful in preparing the compounds of the present invention.

The compounds of the invention can be prepared as a single isomer or a mixture of isomers, including, for example cis-isomers, trans-isomers, diastereomers and stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single isomer. Techniques for inverting or leaving unchanged a particular stereocenter, and those for resolving mixtures of stereoisomers are well known in the art and it is well within the ability of one of skill in the art to choose an appropriate resolution or synthetic method for a particular situation. See, generally, Furniss et al. (eds.), VOGEL'S ENCYCLOPEDIA OF PRACTICAL ORGANIC CHEMISTRY 5$^{TH}$ ED., Longman Scientific an d Technical Ltd., Essex, 1991, pp. 809-816; and Heller, Acc. Chem. Res. 23: 128 (1990).

Scheme 1

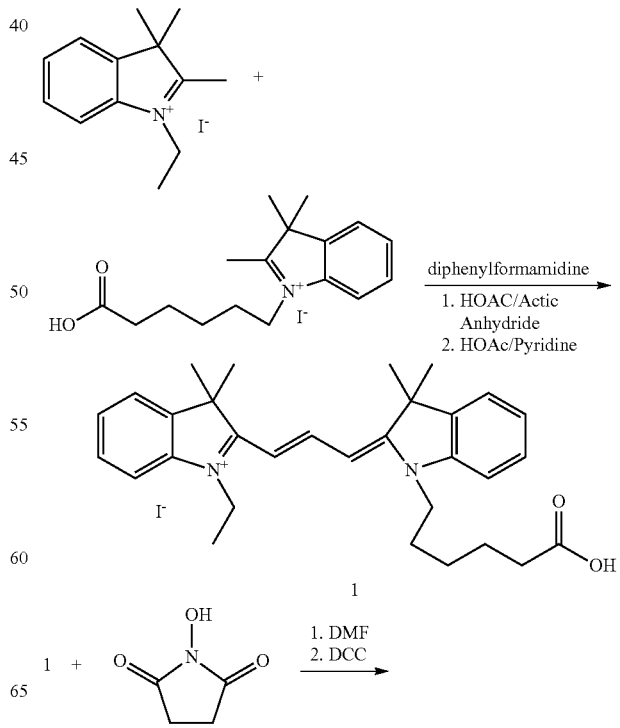

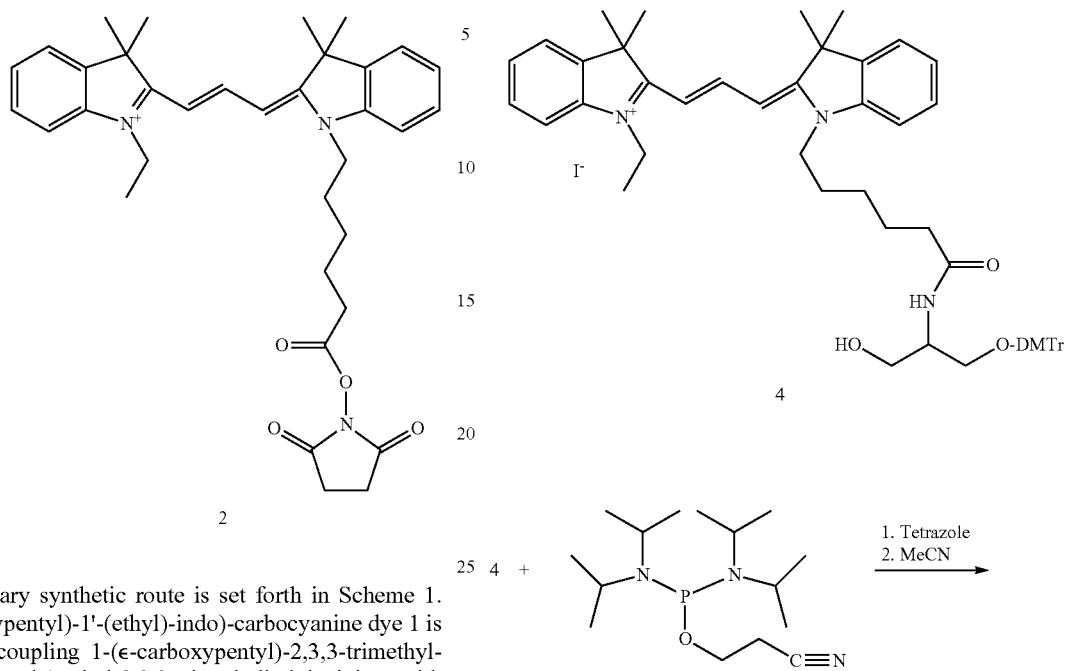

An exemplary synthetic route is set forth in Scheme 1. (1-(ε-Carboxypentyl)-1'-(ethyl)-indo)-carbocyanine dye 1 is prepared by coupling 1-(ε-carboxypentyl)-2,3,3-trimethyl-indoleninium and 1-ethyl-2,3,3-trimethylindoleninium with N,N'-diphenylformamidine. The N-hydroxysucinimide ester of the dye 2 is prepared by the DCC mediated coupling of N-hydroxysuccinimide with 1.

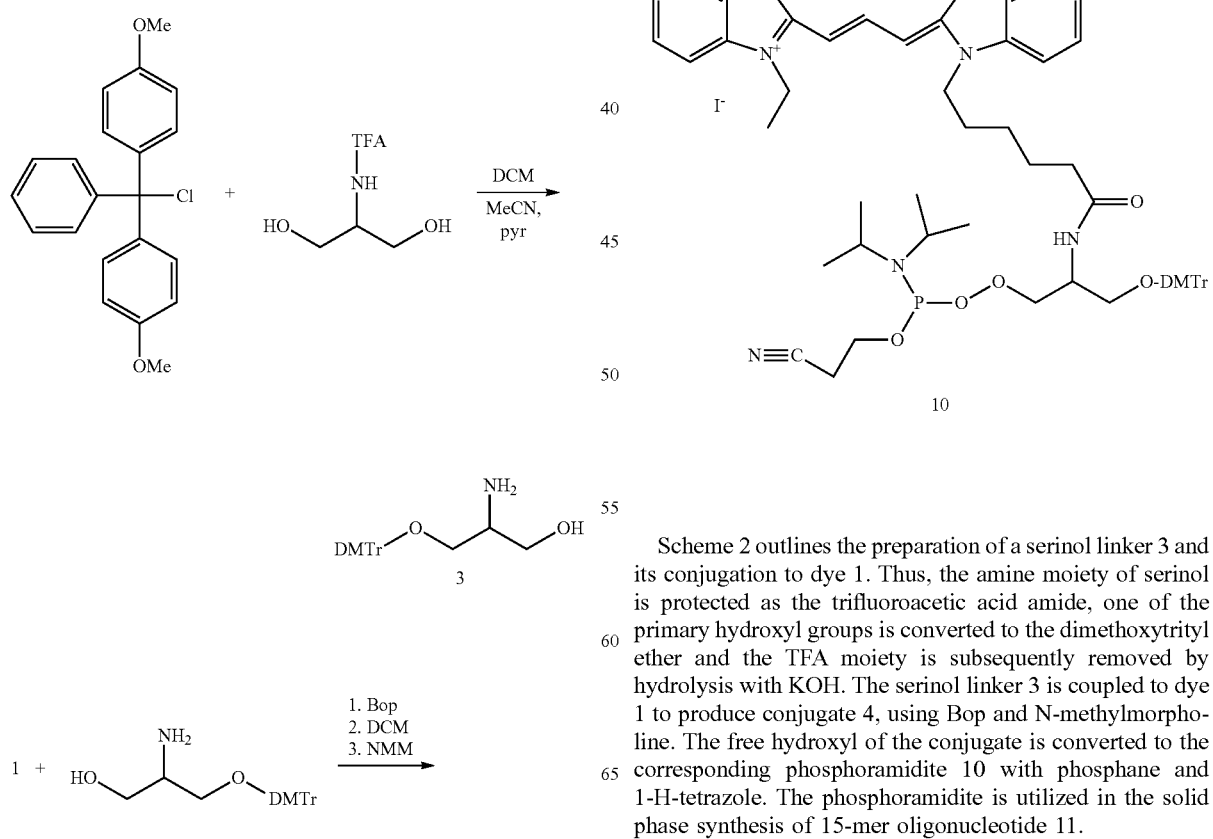

Scheme 2 outlines the preparation of a serinol linker 3 and its conjugation to dye 1. Thus, the amine moiety of serinol is protected as the trifluoroacetic acid amide, one of the primary hydroxyl groups is converted to the dimethoxytrityl ether and the TFA moiety is subsequently removed by hydrolysis with KOH. The serinol linker 3 is coupled to dye 1 to produce conjugate 4, using Bop and N-methylmorpholine. The free hydroxyl of the conjugate is converted to the corresponding phosphoramidite 10 with phosphane and 1-H-tetrazole. The phosphoramidite is utilized in the solid phase synthesis of 15-mer oligonucleotide 11.

Scheme 3

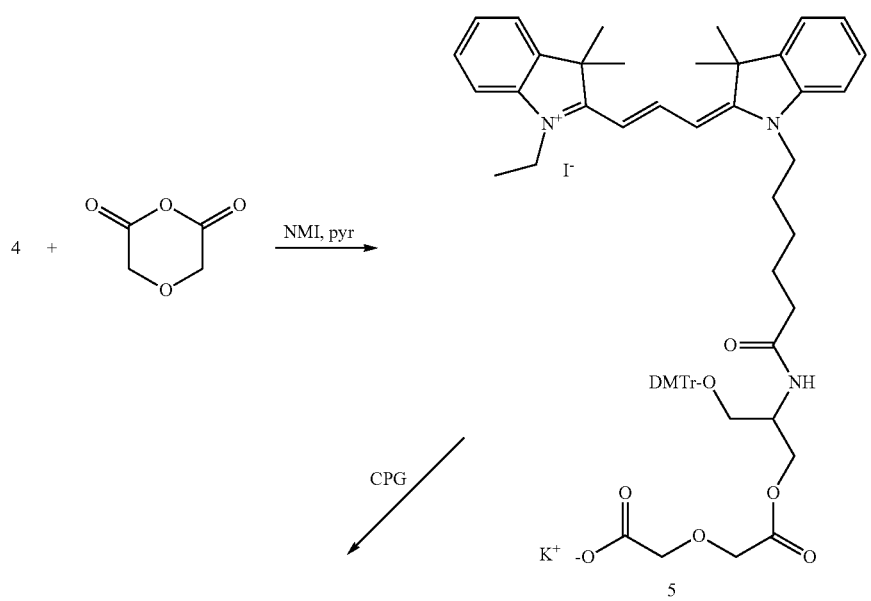

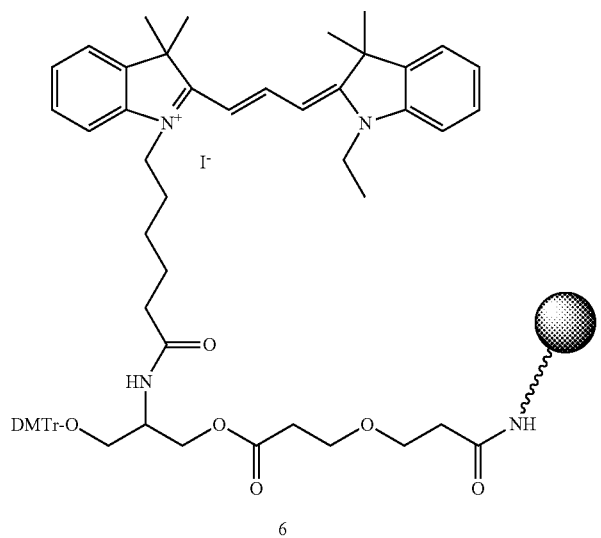

Scheme 3 sets out an exemplary route for preparing a linker arm derivatized dye and its attachment to a solid support. The serinol dye conjugate 4 was acylated with diglycolic anhydride, forming 5. A solid support with a dye of the invention immobilized thereon was prepared by combining 5 with aminopropylated controlled pore glass in the presence of Bop and HOBT.

Scheme 4

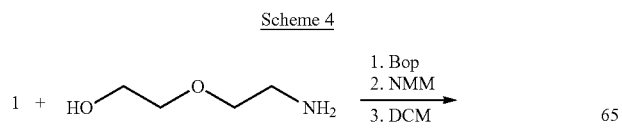

-continued

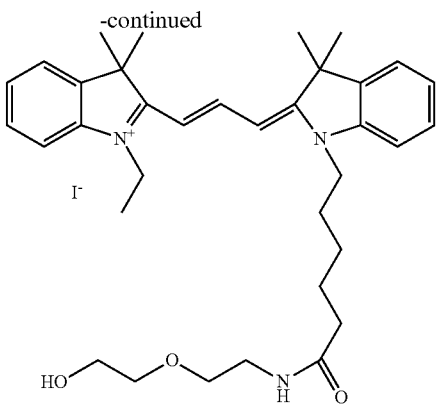

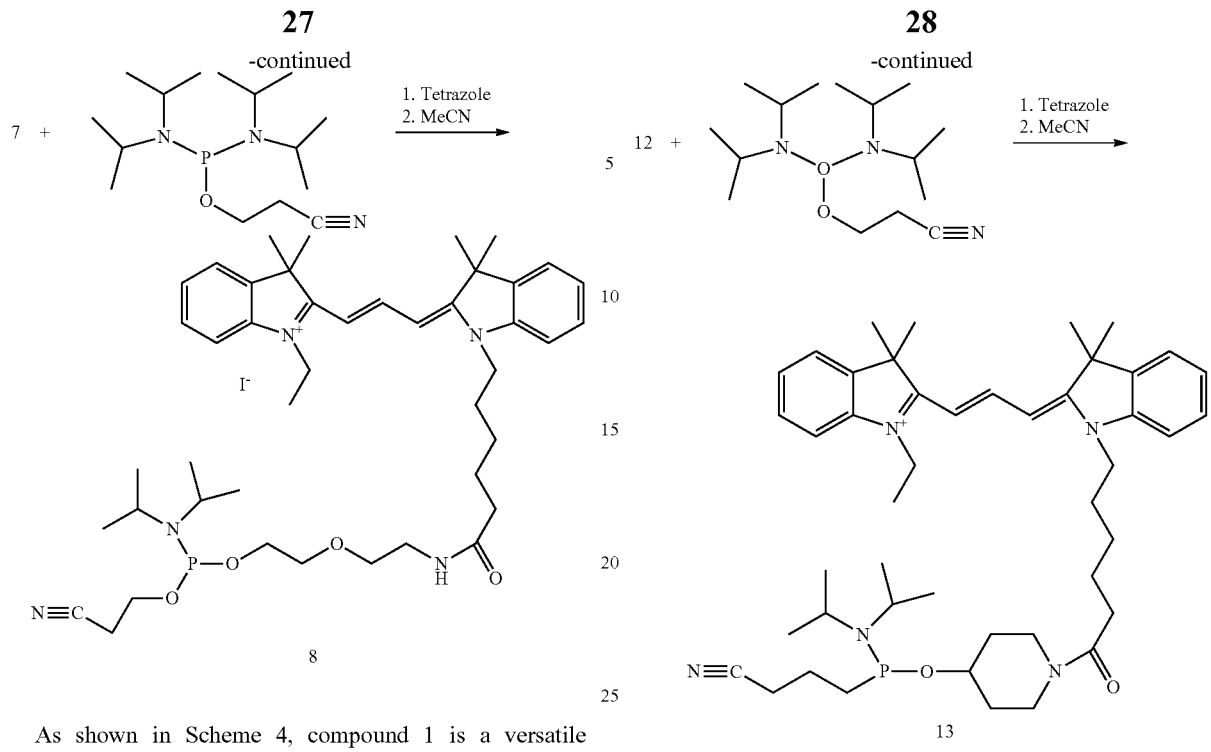

As shown in Scheme 4, compound 1 is a versatile intermediate, allowing access to a variety of linker derivatized cyanine dyes. Thus, 1 is converted to the corresponding 2-(2-aminoethoxy)-ethanol derivative by coupling this moiety to the carboxylic acid moiety of the dye to form 7. The hydroxyl moiety of 7 is converted to a phosphoramidite, affording 8, which is utilized in the solid phase synthesis of 15-mer oligonucleotide 9.

Linkers of use in the invention also include cyclic structures. As shown in Scheme 5, N-hydroxypiperidine is conjugated to 1, forming 12, which is converted to phosphoramidate 13. The phosphoramidate is utilized in the solid phase synthesis of dye conjugated 15-mer oligonucleotide 14.

Another amino-alcohol of use as a linker is 6-amino-1-hexanol, which, as shown in Scheme 6, is coupled to dye 1, forming conjugate 15. The hydroxyl moiety of 15 is converted to the phosphoramidate, providing 16, which is utilized in the preparation of dye conjugated 15-mer oligonucleotide 17.

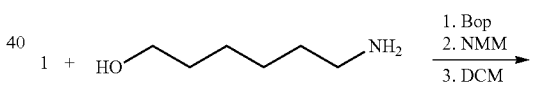

Scheme 6

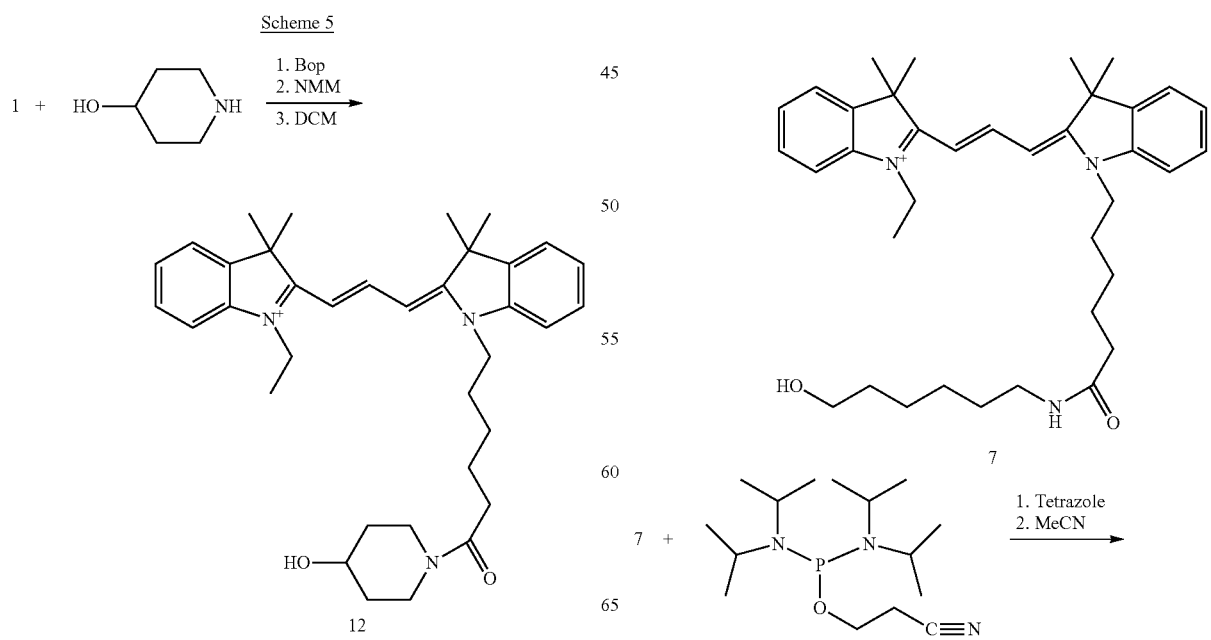

-continued

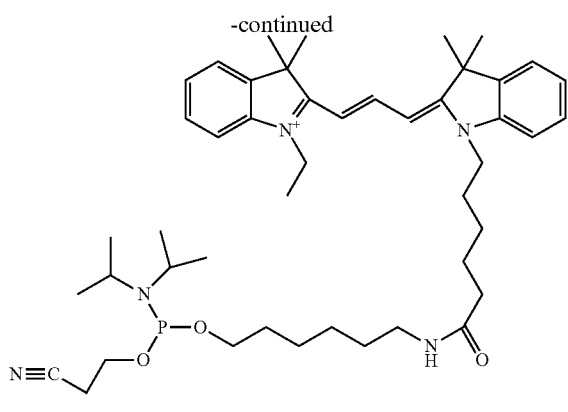

8

Chemical synthesis of the nucleic acid is generally automated and is performed by coupling nucleosides through phosphorus-containing covalent linkages. The most commonly used oligonucleotide synthesis method involved reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. The labels of the present invention can be incorporated during oligonucleotide synthesis using a mono- or bis-phosphoramidite derivative of the fluorescent compound of the invention. Alternatively, the label can be introduced by combining a compound of the invention that includes a reactive functional group with the nucleic acid under appropriate conditions to couple the compound to the nucleic acid. In yet another embodiment, the fluorescent compound is attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners.

In those embodiments of the invention in which the cyanine-based fluorescent compound of the invention is attached to a nucleic acid, the carrier molecule is produced by either synthetic (solid phase, liquid phase or a combination) or enzymatically or by a combination of these processes.

Another synthetic strategy for the preparation of oligonucleotides is the H-phosphonate method (B. Froehler and M. Matteucci, *Tetrahedron Lett., vol* 27, p 469-472, 1986). This method utilizes activated nucleoside H-phosphonate monomers rather than phosphoramidites to create the phosphate internucleotide linkage. In contrast to the phosphoramidite method, the resulting phosphonate linkage does not require oxidation every cycle but instead only a single oxidation step at the end of chain assembly. The H-phosphonate method may also be used to conjugate reporters and dyes to synthetic oligonucleotide chains (N. Sinha and R. Cook, *Nucleic Acids Research*, Vol 16, p. 2659, 1988).

Reactive Functional Groups

The compounds of the invention bear a reactive functional group, which can be located at any position on the molecule. Exemplary species include a reactive functional group as a constituent of at least one of $R^2$ and $R^3$. When the reactive group is attached a substituted or unsubstituted alkyl or substituted or unsubstituted heteroalkyl moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive cyanine-based compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:
(a) carboxyl groups and derivatives thereof including, but not limited to activated esters, e.g., N-hydroxysuccinimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;
(b) hydroxyl groups, which can be converted to esters, sulfonates, phosphoramidates, ethers, aldehydes, etc.
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, allowing derivatization via formation of carbonyl derivatives, e.g., imines, hydrazones, semicarbazones or oximes, or via such mechanisms as Grignard addition or alkyllithium addition;
(f) sulfonyl halide groups for reaction with amines, for example, to form sulfonamides;
(g) thiol groups, which can be converted to disulfides or reacted with acyl halides, for example;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds; and
(k) phosphoramidites and other standard functional groups useful in nucleic acid synthesis.

The reactive functional groups can be chosen such that they do not participate in, or interfere with, the reactions necessary to assemble or utilize the reactive cyanine analogue. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In addition to those embodiments in which a compound of the invention is attached directly to a carrier molecule, the fluorophores can also be attached by indirect means. In this embodiment, a ligand molecule (e.g., biotin) is generally covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, and peroxidases.

Probes

The invention provides probes having a cyanine dye of the invention conjugated to a carrier molecule, for example, a target species (e.g., receptor, enzyme, etc.) a ligand for a target species (e.g., nucleic acid, peptide, etc.), a small molecule (e.g., drug, pesticide, etc.), a solid support and the like. The probes can be used for in vitro and in vivo applications.

An unexpected property of the cyanine dye of the invention is their robustness under a variety of synthetic conditions used to attach the cyanine dye of the invention to a carrier molecule. For example, many of the cyanine dyes of the invention survive the conditions necessary for automated synthesis of nucleic acids without undergoing any substantial degree of degradation or alteration. In contrast, many of art-recognized fluorophores presently in use require the use of special conditions to assemble the carrier molecule to which they are attached, or they have to be attached after the completion of the carrier molecule synthesis. The additional complexity of the synthesis of a probe increases both the duration of the synthesis and its cost.

Small Molecule Probes

The cyanine dyes of the invention can be used as components of small molecule probes. In a preferred design, a small molecule probe includes a cyanine dye of the invention and a second species that alters the luminescent properties of the dyes, e.g., a quencher of fluorescence. In an exemplary embodiment, an agent, such as an enzyme cleaves the cyanine dye of the invention, the quencher or both from the small molecule generating fluorescence in the system under investigation (see, for example, Zlokarnik et al., *Science* 279: 84-88 (1998)).

Nucleic Acid Capture Probes

In one embodiment, an immobilized nucleic acid comprising a cyanine dye of the invention is used as a capture probe. The nucleic acid probe can be used in solution phase or it can be attached to a solid support. The immobilized probes can be attached directly to the solid support or through a linker arm between the support and the cyanine dye or between the support and a nucleic acid residue. Preferably, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length. Exemplary attachment points include the 3'- or 5'-terminal nucleotide of the probe as well as other accessible sites discussed herein.

In yet another preferred embodiment, the solid support is also used as the synthesis support in preparing the probe. The length and chemical stability of the linker between the solid support and the first 3'-unit of nucleic acid (or the cyanine dye) play an important role in efficient synthesis and hybridization of support bound nucleic acids. The linker arm should be sufficiently long so that a high yield (>97%) can be achieved during automated synthesis. The required length of the linker will depend on the particular solid support used. Exemplary linker are from about 6 to about 30 atoms in length. For nucleic acid synthesis, the linker arm is usually attached to the 3'-OH of the 3'-terminus by a cleaveable linkage, e.g., an ester linkage, which can be cleaved with appropriate reagents to free the nucleic acid from the solid support.

Hybridization of a probe immobilized on a solid support generally requires that the probe be separated from the solid support. A preferred linker for this embodiment includes at least about 20 atoms, more preferably at least about 50 atoms.

A wide variety of linkers are known in the art, which may be used to attach the nucleic acid probe to the solid support. The linker may be formed of any moiety or combination of moieties, which does not significantly interfere with the hybridization of the target sequence to the probe attached to the solid support. The linker may be formed of, for example, a homopolymeric nucleic acid, which can be readily added on to the linker by automated synthesis. Alternatively, polymers such as polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkages between the solid support, the linker and the probe are preferably not cleaved during synthesis or removal of base protecting groups under basic conditions at high temperature. These linkages can, however, be selected from groups that are cleavable under a variety of conditions. Examples of presently preferred linkages include carbamate, ester and amide linkages.

Dual Labeled Probes

The present invention also provides dual labeled probes that include both a cyanine dye of the invention and another label. Exemplary dual labeled probes include nucleic acid probes that include a nucleic acid with a cyanine dye of the invention attached thereto. Exemplary probes include both a cyanine dye of the invention and a quencher. The probes are of use in a variety of assay formats. For example, when a nucleic acid singly labeled with a cyanine dye of the invention is the probe, the interaction between the first and second nucleic acids can be detected by observing the interaction between the cyanine dye of the invention and the nucleic acid. Alternatively, the interaction is the quenching by a quencher attached to the second nucleic acid of the fluorescence from a cyanine dye of the invention.

The cyanine dyes of the invention are useful in conjunction with nucleic-acid probes in a variety of nucleic acid amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the cyanine dye of the invention-derivatized nucleic acids can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to nature genetics, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci. USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

In view of the well-developed body of literature concerning the conjugation of small molecules to nucleic acids, many other methods of attaching donor/acceptor pairs to nucleic acids will be apparent to those of skill in the art.

More specifically, there are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Exemplary fluorophores that can be combined in a probe with a cyanine dye of the invention include those set forth in Table 1.

TABLE 1

Suitable moieties that can be selected as donors or acceptors in donor-acceptor energy transfer pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
    coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

As will be apparent to those of skill in the art the methods set forth above are equally applicable to the coupling to a nucleic acid of groups other than the fluorescent compounds of the invention, e.g., quenchers, intercalating agents, hybridization enhancing moieties, minor groove binders, alkylating agents, cleaving agents, etc.

For example, in selected embodiments, the probe includes a metal chelate or a chelating agent attached to the carrier molecule. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, J. R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In a presently preferred embodiment, the chelating agent is a polyaminocarboxylate chelating agent such as ethylenediaminetetraacetic acid (EDTA) or diethylenetriaminepentaacetic acid (DTPA). These chelating agents can be attached to any amine-terminated component of a carrier molecule or a spacer arm, for example, by utilizing the commercially available dianhydride (Aldrich Chemical Co., Milwaukee, Wis.).

The nucleic acids for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linking moiety.

The nucleic acid can comprise DNA, RNA or chimeric mixtures or derivatives or modified versions thereof. Both the probe and target nucleic acid can be present as a single strand, duplex, triplex, etc. Moreover, as discussed above, the nucleic acid can be modified at the base moiety, sugar moiety, or phosphate backbone with other groups such as radioactive labels, minor groove binders, intercalating agents, donor and/or acceptor moieties and the like.

For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, nitroindole, and 2,6-diaminopurine. The cyanine dye of the invention or another probe component can be attached to the modified base.

In another embodiment, the nucleic acid comprises at least one modified sugar moiety selected from the group including, but not limited to, arabinose, 2-fluoroarabinose, xylulose, and hexose. The cyanine dye or another probe component can be attached to the modified sugar moiety.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. The cyanine dye or another probe component can be attached to the modified phosphate backbone.

Phosphodiester linked nucleic acids of the invention can be synthesized by standard methods known in the art, e.g. by use of an automated DNA synthesizer using commercially available amidite chemistries (Ozaki et al., *Nucleic Acids Research,* 20: 5205-5214 (1992); Agrawal et al., *Nucleic Acids Research,* 18: 5419-5423 (1990); Beaucage et al., *Tetrahedron,* 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the quencher moiety is preferably separated from the cyanine dye of the invention by at least about 10 nucleotides, and more preferably by at least about 15 nucleotides. The quencher moiety is preferably attached to either the 3'- or 5'-terminal nucleotides of the probe. The cyanine dye of the invention moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine:water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Peptide Probes

Peptides, proteins and peptide nucleic acids that are labeled with a quencher and a cyanine dye of the invention can be used in both in vivo and in vitro enzymatic assays.

Peptide constructs useful in practicing the invention include those with the following features: i) a quencher; ii) a cyanine dye of the invention; and iii) a cleavage or assembly recognition site for the enzyme. Moreover, the peptide construct is preferably exists in at least one conformation that allows donor-acceptor energy transfer between the cyanine dye of the invention and the quencher when the fluorophore is excited.

In the dual labeled probes of the invention, the donor and acceptor moieties are connected through an intervening linker moiety. The linker moiety, preferably, includes a peptide moiety, but can be or can include another organic molecular moiety, as well. In a preferred embodiment, the linker moiety includes a cleavage recognition site specific for an enzyme or other cleavage agent of interest. A cleavage site in the linker moiety is useful because when a tandem construct is mixed with the cleavage agent, the linker is a substrate for cleavage by the cleavage agent. Rupture of the linker moiety results in separation of the cyanine dye and the quencher. The separation is measurable as a change in donor-acceptor energy transfer. Alternatively, peptide assembly can be detected by an increase in donor-acceptor energy transfer between a peptide fragment bearing a cyanine dye of the invention and a peptide fragment bearing a donor moiety.

When the cleavage agent of interest is a protease, the linker generally includes a peptide containing a cleavage recognition sequence for the protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in AMYLOID PROTEIN PRECURSOR IN DEVELOPMENT, AGING, AND ALZHEIMER'S DISEASE, ed. Masters et al. pp. 190-198 (1994).

Solid Support Immobilized Cyanine Dye Analogues

The cyanine dyes of the invention can be immobilized on substantially any polymer, biomolecule, or solid or semi-solid material having any useful configuration. Moreover, any conjugate comprising one or more cyanine dye of the invention can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a cyanine dye of the invention or a species to which a cyanine dye of the invention is conjugated. For clarity of illustration, the following discussion focuses on attaching a reactive cyanine dye of the invention to a solid support. The following discussion is also broadly relevant to attaching to a solid support a species that includes within its structure a cyanine dye of the invention.

The cyanine dyes of the invention are preferably attached to a solid support by forming a bond between a reactive group on the cyanine dye of the invention and a reactive group on the surface of the solid support, thereby derivatizing the solid support with one or more cyanine dye of the invention. Alternatively, the reactive group on the cyanine dye of the invention is coupled with a reactive group on a linker arm attached to the solid support. The bond between the solid support and the cyanine dye of the invention is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Moreover, for applications in which an appropriate solid support is not commercially available, a wide variety of reaction types are available for the functionalization of a solid support surface. For example, supports constructed of a plastic such as polypropylene, can be surface derivatized by chromic acid oxidation, and subsequently converted to hydroxylated or aminomethylated surfaces. The functionalized support is then reacted with a cyanine dye of the invention of complementary reactivity, such as a cyanine dye of the invention active ester, acid chloride or sulfonate ester, for example. Supports made from highly crosslinked divinylbenzene can be surface derivatized by chloromethylation and subsequent functional group manipulation. Additionally, functionalized substrates can be made from etched, reduced polytetrafluoroethylene.

When the support is constructed of a siliceous material such as glass, the surface can be derivatized by reacting the surface Si—OH, SiO—H, and/or Si—Si groups with a functionalizing reagent.

In a preferred embodiment, wherein the substrates are made from glass, the covalent bonding of the reactive group to the glass surface is achieved by conversion of groups on the substrate's surface by a silicon-modifying reagent such as:

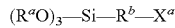

where $R^a$ is an alkyl group, such as methyl or ethyl, $R^b$ is a linking group between silicon and $X^a$, and $X^a$ is a reactive group or a protected reactive group. Silane derivatives having halogens or other leaving groups beside the displayed alkoxy groups are also useful in the present invention. Exemplary linking groups include those that include substituted or unsubstituted alkyl and substituted or unsubstituted heteroalkyl groups.

In another preferred embodiment, the reagent used to functionalize the solid support provides for more than one reactive group per each reagent molecule. Using reagents, such as the compound below, each reactive site on the substrate surface is, in essence, "amplified" to two or more functional groups:

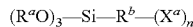

where $R^a$ is an alkyl group (e.g., methyl, ethyl), $R^b$ is a linking group between silicon and $X^a$, $X^a$ is a reactive group or a protected reactive group and n is an integer between 2 and 50, and more preferably between 2 and 20. The amplification of a cyanine dye of the invention by its attachment to a silicon-containing substrate is intended to be exemplary of the general concept of amplification. This amplification strategy is equally applicable to other aspects of the invention in which a cyanine dye of the invention is attached to another molecule or solid support.

A number of siloxane functionalizing reagents can be used, for example:
1. Hydroxyalkyl siloxanes (Silylate surface, functionalize with diborane, and $H_2O_2$ to oxidize to the alcohol)
   a. allyl trichlorosilane→→3-hydroxypropyl
   b. 7-oct-1-enyl trichlorchlorosilane→→8-hydroxyoctyl;
2. Diol (dihydroxyalkyl)siloxanes (silylate surface and hydrolyze to diol)
   a. (glycidyl trimethoxysilane→(2,3-dihydroxypropyloxy)propyl;
3. Aminoalkyl siloxanes (amines requiring no intermediate functionalizing step);
   a. 3-aminopropyl trimethoxysilane→aminopropyl
4. Dimeric secondary aminoalkyl siloxanes
   a. bis(3-trimethoxysilylpropyl)amine→bis(silyloxylpropyl)amine.

It will be apparent to those of skill in the art that an array of similarly useful functionalizing chemistries is available when support components other than siloxanes are used. Thus, for example alkyl thiols (e.g., self-assembled monolayers), functionalized as discussed above in the context of siloxane-modifying reagents, can be attached to metal films and subsequently reacted with a cyanine dye of the invention to produce the immobilized compound of the invention.

Exemplary groups of use for $R^b$ in the above described embodiments of the present invention include, but are not limited to, substituted or unsubstituted alkyl (e.g., substituted or unsubstituted arylalkyl, alkylamino, alkoxy), substituted or unsubstituted aryl (e.g., substituted or unsubstituted arylalkyl, aryloxy and aryloxyalkyl), acyl (e.g., acylamino, acyloxy), mercapto, saturated or unsaturated cyclic hydrocarbyl, substituted or unsubstituted heteroaryl (e.g., substituted or unsubstituted heteroarylalkyl), substituted or unsubstituted heterocycloalkyl, and combinations thereof.

Acrylamide-Immobilized Probes

In another exemplary embodiment, a species conjugated to a cyanine dye of the invention is immobilized within a matrix, such as an acrylamide matrix. In a preferred embodiment, the immobilization is accomplished in conjunction with the "acrydite" process (see, Rehman et al., *Nucleic Acids Research*, 27: 649-655 (1999)). The acrydite method allows immobilization of alkene labeled probes within a polymerized polyacrylamide network. When target mixes are run past the immobilized probe band under electrophoresis conditions, the target nucleic acid is captured substantially quantitatively. However, detection of this event currently requires a second probe. In one embodiment, probes bearing a cyanine dye of the invention, and/or a fluorophore, are immobilized in an acrylamide matrix and subsequently contacted with the target mix. By using fluorescent probes as capture probes, signals from target mixes can be directly detected in real time.

Microarrays

The present invention also provides microarrays including immobilized cyanine dye of the invention and compounds (e.g., peptides, nucleic acids, bioactive agents, etc.) functionalized with cyanine dye of the invention. Moreover, the invention provides methods of interrogating microarrays using probes that are functionalized with cyanine dye of the invention. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics*, 21:48-50 (1999). The discussion that follows focuses on the use of a cyanine dye of the invention in conjunction with nucleic acid microarrays. This focus is intended to be illustrative and does not limit the scope of materials with which this aspect of the present invention can be practiced.

In another preferred embodiment, the compounds of the present invention are utilized in a microarray format. The cyanine dye of the invention, or species bearing cyanine dye of the invention can themselves be components of a microarray or, alternatively they can be utilized as a tool to screen components of a microarray.

Thus, in a preferred embodiment, the present invention provides a method of screening a microarray. The method includes contacting the members of the microarray with, for example, a cyanine dye of the invention-bearing probe and interrogating the microarray for regions of fluorescence. In an exemplary embodiment, fluorescent regions are indicative of the presence of an interaction between the cyanine dye of the invention-bearing probe and a microarray component.

In another exemplary embodiment, the array comprises an immobilized cyanine-bearing donor-acceptor energy transfer probe. In this embodiment, when the probe interacts (e.g., hybridizes) with its target, energy transfer between the cyanine and a quencher moiety is disrupted and the cyanine dye fluoresces. Such arrays are easily prepared and read, and can be designed to give quantitative data. Arrays comprising a cyanine-bearing probe are valuable tools for expression analysis and clinical genomic screening.

In another embodiment, the immobilized cyanine-bearing probe is not a donor-acceptor energy transfer probe. A microarray based on such as format can be used to probe for the presence of interactions between an analyte and the immobilized probe by, for example, observing the alteration of analyte fluorescence upon interaction between the probe and analyte.

Exemplary microarrays comprise n regions of identical or different species (e.g., nucleic acid sequences, bioactive agents). In a preferred embodiment, n is a number from 2 to 100, more preferably, from 10 to 1,000, and more preferably from 100 to 10,000. In a still further preferred embodiment, the n regions are patterned on a substrate as n distinct locations in a manner that allows the identity of each of the n locations to be ascertained.

In yet another embodiment, the invention also provides a method for preparing a microarray of n cyanine-bearing probes. The method includes attaching cyanine dye-bearing probes to selected regions of a substrate. A variety of methods are currently available for making arrays of biological macromolecules, such as arrays nucleic acid molecules. The following discussion focuses on the assembly of a microarray of cyanine-bearing probes, this focus is for reasons of brevity and is intended to be illustrative and not limiting.

One method for making ordered arrays of a cyanine-bearing probe on a substrate is a "dot blot" approach. In this method, a vacuum manifold transfers a plurality, e.g., 96, aqueous samples of probes from 3 millimeter diameter wells to a substrate. The probe is immobilized on the porous membrane by baking the membrane or exposing it to UV radiation. A common variant of this procedure is a "slot-blot" method in which the wells have highly-elongated oval shapes.

Another technique employed for making ordered arrays of probes uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGER-PRINTING IN GENOME MAPPING AND SEQUENCING, GENOME ANALYSIS, Vol. 1, Davies et al, Eds., Cold Springs Harbor Press, pp. 39-81 (1990).

An alternate method of creating ordered arrays of probes is analogous to that described by Pirrung et al. (U.S. Pat. No. 5,143,854, issued 1992), and also by Fodor et al., (*Science*, 251: 767-773 (1991)). This method involves synthesizing different probes at different discrete regions of a particle or other substrate. This method is preferably used with relatively short probe molecules, e.g., less than 20 bases. A related method has been described by Southern et al. (*Genomics*, 13: 1008-1017 (1992)).

Khrapko, et al., *DNA Sequence*, 1: 375-388 (1991) describes a method of making an nucleic acid matrix by spotting DNA onto a thin layer of polyacrylamide. The spotting is done manually with a micropipette.

The substrate can also be patterned using techniques such as photolithography (Kleinfield et al., *J. Neurosci.* 8:4098-120 (1998)), photoetching, chemical etching and microcontact printing (Kumar et al., *Langmuir* 10:1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y., *J. Am. Chem. Soc.* 117:3274-75 (1995). Similarly, using photolithography, patterns with features as small as 1 µm are produced. See, Hickman et al., *J. Vac. Sci. Technol.* 12:607-16 (1994). Patterns which are useful in the present invention include those which include features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the probes. In general, each of these substrate features is isolated from the other wells by a raised wall or partition and the wells do not readily fluidically communicate. Thus, a particle, reagent or other substance, placed in a particular well remains substantially confined to that well. In another preferred embodiment, the patterning allows the creation of channels through the device whereby an analyte or other substance can enter and/or exit the device.

In another embodiment, the probes are immobilized by "printing" them directly onto a substrate or, alternatively, a "lift off" technique can be utilized. In the lift off technique, a patterned resist is laid onto the substrate, and a probe is laid down in those areas not covered by the resist and the resist is subsequently removed. Resists appropriate for use with the substrates of the present invention are known to those of skill in the art. See, for example, Kleinfield et al., *J. Neurosci.* 8:4098-120 (1998). Following removal of the photoresist, a second probe, having a structure different from the first probe can be bonded to the substrate on those areas initially covered by the resist. Using this technique, substrates with patterns of probes having different characteristics can be produced. Similar substrate configurations are accessible through microprinting a layer with the desired characteristics directly onto the substrate. See, Mrkish et al. *Ann. Rev. Biophys. Biomol. Struct.* 25:55-78 (1996).

Linkers

As used herein, the term "linker," refers to a constituent of a conjugate between a cyanine dye and a carrier molecule. The linker is a component of the cyanine dye, the carrier molecule or it is a reactive cross-linking species that reacts with both the carrier molecule and the cyanine dye. The linker groups can be hydrophilic (e.g., tetraethylene glycol, hexaethylene glycol, polyethylene glycol) or they can be hydrophobic (e.g., hexane, decane, etc.). Exemplary linkers include substituted or unsubstituted $C_6$-$C_{30}$ alkyl groups, polyols (e.g., glycerol), polyethers (e.g., poly(ethyleneglycol)), polyamines, amino acids (e.g., polyaminoacids), saccharides (e.g., polysaccharides) and combinations thereof.

In an exemplary embodiment, the linker joins donor and/or acceptor moieties and other groups to a nucleic acid, peptide or other component of a probe. In a further exemplary embodiment, using a solid support, the immobilized construct includes a linker attached through the solid support and also to the cyanine dye.

In certain embodiments, it is advantageous to have the donor and/or acceptor moieties of the probe attached to a carrier molecule by a group that provides flexibility and distances the linked species from the carrier molecule. Using linker groups, the properties of the donor and/or acceptor moiety is modulated. Properties that are usefully controlled include, for example, hydrophobicity, hydrophilicity, surface-activity, the distance of the quencher and/or cyanine dye of the invention moiety from the other probe components (e.g., carrier molecule) and the distance of the quencher from the cyanine dye of the invention.

In an exemplary embodiment, the linker serves to distance the cyanine dye of the invention from a nucleic acid to which it is attached. Linkers with this characteristic have several uses. For example, a cyanine dye of the invention held too closely to the nucleic acid may not interact with the quencher group, or it may interact with too low of an affinity. When a cyanine dye of the invention is itself sterically demanding, the interaction leading to quenching can be undesirably weakened, or it may not occur at all, due to a sterically induced hindering of the approach of the two components.

When the construct comprising the cyanine dye is immobilized by attachment to, for example, a solid support, the construct can also include a linker moiety placed between the reactive group of the solid support and the cyanine analogue, or other probe component bound to the solid support.

In yet a further embodiment, a linker group used in the probes of the invention is provided with a group that can be cleaved to release a bound moiety, e.g., a cyanine dye of the invention, quencher, minor groove binder, intercalating moiety, and the like from the polymeric component. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover a broad range of cleavable, bifunctional (both homo- and hetero-bifunctional) linker arms is commercially available from suppliers such as Pierce. Exemplary cleaveable groups are those cleaved by light, e.g., nitrobenzyl derivatives, phenacyl groups, benzoin esters; hydrolysis, e.g., esters, carbonates; changes in pH, etc.

The Methods

In another aspect embodiment, the present invention provides a method for detecting a target species in an assay mixture or other sample. The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

An exemplary method uses a cyanine dye of the invention or a conjugate thereof to detect a nucleic acid target sequence. The method includes: (a) contacting the target sequence with a detector nucleic acid that includes a cyanine dye of the invention and a quencher; (b) hybridizing the detector nucleic acid to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a quencher; and ii) a cyanine dye of the invention. Moreover, prior to its hybridization to a complementary sequence, the detector nucleic acid is preferably in a conformation that allows donor-acceptor energy transfer between the quencher and the cyanine dye of the invention when the fluorophore is excited. Furthermore, in the methods described in this section, a change in fluorescence is detected as an indication of the presence of the target sequence. The change in fluorescence is preferably detected in real time.

Presently preferred nucleic acid probes do not require the carrier molecule to adopt a secondary structure for the probe to function. Exemplary probes according to this motif include a quencher moiety that includes the diazo-linked quenchers described in co-pending, commonly assigned U.S. patent application Ser. No. 09/567,863 (WO 01/86001) or the conformationally assisted probes disclosed in U.S. patent application Ser. No. 09/591,185.

In other methods described in this section, the detector nucleic acid can assume substantially any intramolecularly associated secondary structure, e.g., hairpins, stem-loop structures, pseudoknots, triple helices and conformationally assisted structures. Moreover, the intramolecularly base-paired secondary structure preferably comprises a portion of the target binding sequence.

In another aspect, the invention provides a method for detecting amplification of a target sequence. The method includes the use of an amplification reaction including the following steps: (a) hybridizing the target sequence and a detector nucleic acid that includes a cyanine dye of the invention. The detector nucleic acid preferably includes a single-stranded target binding sequence and an intramolecularly associated secondary structure 5' to the target binding sequence. At least a portion of the detector sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In yet a further aspect, the invention provides a method of ascertaining whether a first nucleic acid and a second nucleic acid hybridize. In this method, the first nucleic acid includes a cyanine dye of the invention. The method includes: (a)

contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

In general, to determine the concentration of a target molecule, e.g., a nucleic acid, it is preferable to first obtain reference data in which constant amounts of probe are contacted with varying amounts of target. The fluorescence emission of each of the reference mixtures is used to derive a graph or table in which target concentration is compared to fluorescence emission. For example, a probe that hybridizes to a nucleic acid ligand and has a stem-loop architecture with the 5' and 3' termini being the sites of quencher and cyanine labeling, can be used to obtain such reference data. The value of the fluorescence emission is then compared with the reference data to obtain the concentration of the target in the test mixture.

The cyanine dyes and their conjugates described herein can be used in substantially any nucleic acid probe format now known or later discovered. For example, the cyanine dyes of the invention can be incorporated into probe motifs, such as Taqman™ probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. patent application Ser. No. 09/591,185), peptide nucleic acid (PNA)-based light up probes (Kubista et al., WO 97/45539, December 1997), double-strand specific DNA dyes (Higuchi et al, *Bio/Technology* 10: 413-417 (1992), Wittwer et al, *BioTechniques* 22: 130-138 (1997)) and the like. These and other probe motifs with which the present cyanine dyes can be used are reviewed in NONISOTOPIC DNA PROBE TECHNIQUES, Academic Press, Inc. 1992.

Peptides, proteins and peptide nucleic acids that are labeled with a quencher and a cyanine dye of the invention can be used in both in vivo and in vitro enzymatic assays.

Thus, in another aspect, the present invention provides a method for determining whether a sample contains an enzyme. The method comprises: (a) contacting the sample with a peptide construct that includes a cyanine dye of the invention; (b) exciting the fluorophore; and (c) determining a fluorescence property of the sample, wherein the presence of the enzyme in the sample results in a change in the fluorescence property.

Peptide constructs useful in practicing the invention include those with the following features: i) a quencher; ii) a cyanine dye of the invention; and iii) a cleavage or assembly recognition site for the enzyme. Moreover, the peptide construct preferably exists in at least one conformation that allows donor-acceptor energy transfer between the cyanine dye of the invention and the quencher when the fluorophore is excited.

When the probe is used to detect an enzyme, such as a degradative enzyme (e.g., protease), and a degree of donor-acceptor energy transfer that is lower than an expected amount is observed, this is generally indicative of the presence of an enzyme. The degree of donor-acceptor energy transfer in the sample can be determined, for example, as a function of the amount of fluorescence from the donor moiety, the amount of fluorescence from the acceptor moiety, the ratio of the amount of fluorescence from the donor moiety to the amount of fluorescence from the acceptor moiety or the excitation state lifetime of the donor moiety.

The assay also is useful for determining the amount of enzyme in a sample. For example, by determining the degree of donor-acceptor energy transfer at a first and second time after contact between the enzyme and the tandem construct, and determining the difference in the degree of donor-acceptor energy transfer. The difference in the degree of donor-acceptor energy transfer reflects the amount of enzyme in the sample.

The assay methods also can also be used to determine whether a compound alters the activity of an enzyme, i.e., screening assays. Thus, in a further aspect, the invention provides methods of determining the amount of activity of an enzyme in a sample from an organism. The method includes: (a) contacting a sample comprising the enzyme and the compound with a peptide construct that includes a cyanine dye of the invention; (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

In a preferred embodiment, the amount of enzyme activity in the sample is determined as a function of the degree of donor-acceptor energy transfer in the sample and the amount of activity in the sample is compared with a standard activity for the same amount of the enzyme. A difference between the amount of enzyme activity in the sample and the standard activity indicates that the compound alters the activity of the enzyme.

Representative enzymes with which the present invention can be practiced include, for example, trypsin, enterokinase, HIV-1 protease, prohormone convertase, interleukin-1b-converting enzyme, adenovirus endopeptidase, cytomegalovirus assemblin, leishmanolysin, β-secretase for amyloid precursor protein, thrombin, renin, angiotensin-converting enzyme, cathepsin-D and a kininogenase, and proteases in general.

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that affect the activity of proteases are natural subjects of combinatorial chemistry. Screening compounds produced by combinatorial chemistry requires convenient enzymatic assays.

The most convenient assays for proteases are based on donor-acceptor energy transfer from a donor fluorophore to a quencher placed at opposite ends of a short peptide chain containing the potential cleavage site (see, Knight C. G., *Methods in Enzymol.* 248:18-34 (1995)). Proteolysis separates the fluorophore and quencher, resulting in increased intensity in the emission of the donor fluorophore. Existing protease assays use short peptide substrates incorporating unnatural chromophoric amino acids, assembled by solid phase peptide synthesis.

Assays of the invention are also useful for determining and characterizing substrate cleavage sequences of proteases or for identifying proteases, such as orphan proteases. In one embodiment the method involves the replacement of a defined linker moiety amino acid sequence with one that contains a randomized selection of amino acids. A library of fluorescent cyanine dye probes, wherein the cyanine dyes of the invention are linked by a randomized peptide linker moiety, which can be generated using recombinant engineering techniques or synthetic chemistry techniques. Screening the members of the library can be accomplished by measuring a signal related to cleavage, such as donor-acceptor energy transfer, after contacting the cleavage enzyme with each of the library members of the tandem fluorescent peptide construct. A degree of donor-acceptor energy transfer that is lower than an expected amount indicates the presence of a linker sequence that is cleaved by the enzyme. The degree of donor-acceptor energy transfer in the sample can be determined, for example, as a function of the amount of fluorescence from the donor moiety, the amount of fluorescence from the acceptor donor moiety, or the ratio of the amount of fluorescence from the donor moiety to the amount of fluorescence from the acceptor moiety or the excitation state lifetime of the donor moiety.

Multiplex Analyses

In another exemplary embodiment, the cyanine dyes of the invention are utilized as a component of one or more probes used in a multiplex assay for detecting one or more species in a mixture.

Probes that include a cyanine dye are particularly useful in performing multiplex-type analyses and assays. In a typical multiplex analysis, two or more distinct species (or regions of one or more species) are detected using two or more probes, wherein each of the probes is labeled with a different fluorophore, quencher or fluorophore/quencher pair. Preferred species used in multiplex analyses relying on donor-acceptor energy transfer meet at least two criteria: the fluorescent species is bright and spectrally well resolved; and the energy transfer between the fluorescent species and the quencher is efficient.

Thus, in a further embodiment, the invention provides a mixture comprising at least a first carrier molecule and a second carrier molecule. The first carrier molecule has covalently bound thereto a first quencher and a first cyanine dye of the invention. An exemplary quencher has a structure that includes at least three radicals selected from aryl, substituted aryl, heteroaryl, substituted heteroaryl and combinations thereof. At least two of the radicals are covalently linked via an exocyclic diazo bond. The mixture also includes a second carrier molecule. The fluorophore, quencher or both the fluorophore and quencher attached to the second carrier molecule is different than that attached to the first nucleic acid.

The cyanine dye of the invention allows for the design of multiplex assays in which more than one quencher structure is used in the assay. In one exemplary assay, at least two distinct cyanine dyes of the invention are used with a common quencher structure. The quencher(s) can be bound to the same molecule as the cyanine dye of the invention or to a different molecule. Moreover, the carrier molecules of use in a particular assay system can be the same or different.

In addition those embodiment described above, the present invention also provides a method for detecting or quantifying a particular molecular species. The method includes: (a) contacting the species with a mixture such as that described above; and (b) detecting a change in a fluorescent property of one or more component of the mixture, the molecular species or a combination thereof, thereby detecting or quantifying the molecular species.

Because the present invention provides readily available cyanine dyes, which can be tuned to emit fluorescence of a desired wavelength, the compounds of the invention are particularly well suited for use in multiplex applications. Access to cyanine dyes of the invention having a range of emission characteristics allows for the design of donor-acceptor energy transfer probes in which the acceptor absorbance properties and the emission properties of the cyanine are substantially matched, thereby providing a useful level of spectral overlap. Moreover, the cyanine dyes of the invention provide access to probes that emit light at different wavelengths allows the probes to be spectrally resolved, which is desirable for multiplex analysis.

The simultaneous use of two or more probes using donor-acceptor energy transfer is known in the art. For example, multiplex assays using nucleic acid probes with different sequence specificities have been described. Fluorescent probes have been used to determine whether an individual is homozygous wild type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228-1229 (1998)). The presence of only a fluorescein signal indicates that the individual is wild type, and the presence of rhodamine signal only indicates that the individual is a homozygous mutant. The presence of both rhodamine and fluorescein signal is diagnostic of a heterozygote. Tyagi et al. *Nature Biotechnology* 16: 49-53 (1998)) have described the simultaneous use of four differently labeled molecular beacons for allele discrimination, and Lee et al., *BioTechniques* 27: 342-349 (1999) have described seven color homogenous detection of six PCR products. The compounds of the invention are of use in such methods.

The quenchers of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., Salmonella), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

Kits

In another aspect, the present invention provides kits containing one or more of the cyanine dye of the invention or a conjugate thereof. In one embodiment, a kit includes a reactive cyanine dye of the invention and directions for attaching this derivative to another molecule. In another embodiment, the kit includes a cyanine-labeled nucleic acid that optionally is also labeled with a quencher and directions for using this nucleic acid in one or more assay format. Other formats for kits will be apparent to those of skill in the art and are within the scope of the present invention.

The materials and methods of the present invention are further illustrated by the examples that follow. These examples are offered to illustrate, but not to limit the claimed invention.

The following examples are provided by way of illustration only and not by way of limitation. Those of skill in the art will readily recognize a variety of non-critical parameters that could be changed or modified to yield essentially similar results.

EXAMPLES

Example 1

1.1 Preparation of (1-(ε-carboxypentyl)-1'-(ethyl)-indo)-carbocyanine dye 1

1-(ε-Carboxypentyl)-2,3,3-trimethylindoleninium and 1-ethyl-2,3,3-trimethylindoleninium where prepared as described by Mujumdar et al., *Bioconjugate Chemistry*, 4(2):105-111 (1993).

1-(ε-Carboxypentyl)-2,3,3-trimethylindoleninium (2 g, 5.65 mmol) and N,N'-diphenylformamidine (1.5 g, 7.64 mmol) were combined with 1:1 acetic acid/acetic anhydride (20 mL) under argon in a 50 mL round-bottom flask. The mixture was heated to light reflux (~120° C.) and maintained overnight with stirring. The mixture was cooled and the solvents were removed by rotary evaporation, which was followed by high vacuum drying. The residue was redissolved in 1:1 acidic acid/pyridine (100 mL) and transferred to a 250 mL round-bottom flask. The mixture was heated to reflux with stirring under argon. 1-Ethyl-2,3,3-trimethylindoleninium (2 g, 6.3 mmol) was slowly added and the resulting mixture was refluxed for 2 h, then cooled and the solvents were removed. The residue was dissolved in dichloromethane (DCM) and the organic layer was washed repeatedly with water. The organic layer was separated and dried with magnesium sulfate ($MgSO_4$). The dried organic layer was filtered, the solvent was removed and the residue was vacuum dried to yield a dark red solid. The crude product was submitted to column chromatography on alumina, eluted with an isocratic mixture of 2% methanol (MeOH), 0.5% pyridine and 97.5% dichloromethane. Yield 2.59 g, 76%

1.2 Preparation of N-hydroxysuccinimide ester 2

Compound 1 (1 g, 1.7 mmol) was dissolved in N,N-dimethylformamide (DMF) (10 mL) in a 25 mL round-bottom flask. 1-Hydroxysuccinimide (0.3 g, 2.6 mmol) and dicyclohexylcarbodiimide (DCC) (0.55 g, 2.6 mmol) dissolved in DMF (3 mL) were added drop-wise with stirring. The mixture was maintained overnight and filtered to remove the urea. The urea was washed with DMF. The solvents were removed by rotary evaporation. The residue was dissolved in dichloromethane and washed with water 3 times. The organic layer was dried over $MgSO_4$, filtered and the solvent removed. The residue was vacuum dried to a dark red solid. The product, 2, was used without further purification. Yield 0.94 g, 98%

1.2 Preparation of 1-O-(4,4'-dimethoxytrityl)-2-amino-propan-3-ol 3

Serinol (11.2 g, 123 mmol) and methyl trifluoroacetate (32 mL, 318 mmol) in methanol (110 mL) were stirred overnight. The solvent was evaporated and the residue was co-evaporated twice from pyridine. The resulting residue was again dissolved in pyridine (50 mL). 4,4'-dimethoxytrityl chloride (ChemGenes) (21.0 g, 62 mmol) was dissolved in pyridine (100 mL). The resulting solution was added to the serinol-pyridine mixture drop-wise over 1 hour under argon and the mixture was stirred overnight. The solvents were evaporated and the residue was dissolved in ethyl acetate (200 mL). The organic layer was washed with saturated aqueous $NaHCO_3$ (2×200 mL) and saturated aqueous $KHPO_4$. The organic layer was separated, dried over $MgSO_4$, gravity filtered and evaporated to half its original volume. The mixture was purified on silica gel (1200 cc), eluted with 25-60% ethyl acetate+1% triethylamine in petroleum ether. Fractions containing pure mono-DMT adduct, determined by TLC in 35% ethyl acetate+1% triethylamine in petroleum ether, were pooled and the solvents were evaporated. The product was dissolved in THF (250 mL) and 1 M aqueous KOH (250 mL) was added. The mixture was stirred overnight. TLC in 50% ethyl acetate: 1% triethylamine: 49% petroleum ether showed the hydrolysis was complete. Ethyl acetate (100 mL) was added to the reaction mixture to separate the layers. The aqueous layer was extracted with ethyl acetate (2×100 mL). The combined organic layers were evaporated and the residue was dissolved in ethyl acetate (250 mL). The organic layer was washed with saturated aqueous $KHPO_4$ (250 mL), dried over $MgSO_4$, gravity filtered and evaporated to yield 14.7 g (30%) of 3 as a white foam.

1.3 Preparation of Serinol Cyanine Dye 4 by Conjugation of 1 with 3

Compound 1 (2.5 g, 4.2 mmol) was combined with benzotriazol-1-yloxytris(dimethylamino)-phosphonium hexafluorophosphate (Bop) (2.8 g, 6.3 mmol) in dichloromethane (75 mL). N-methylmorpholine (NMM) (1.4 mL) was added and the resulting mixture was stirred for 10 minutes. Compound 3 (2.3 g, 5.8 mmol) was dissolved in dichloromethane (50 mL) and the mixture was added dropwise to mixture including 1. The resulting mixture was stirred for two hours, and was transferred to a separatory funnel, where it was washed once with 1M citric acid, once with water and once with saturated sodium hydrogen carbonate (aq). The organic layer was dried over $MgSO_4$, filtered and the solvent was removed. The residue was vacuum dried to yield dark red solid. The crude product was purified by column chromatography on alumina, eluted with a gradient that ranged from 1% MeOH: 0.5% pyridine: 98.5% dichloromethane to 2.5% MeOH: 0.5% pyridine: 97% dichloromethane. Pure product fractions where pooled together evaporated to dryness to give a dark red solid. Yield 1.76 g, 43%

1.4 Preparation of Cyanine Dye 5 by Reaction of 4 with Diglycolic Anhydride Compound 4 (1.7 g, 1.8 mmol) was dissolved in pyridine (50 mL) in a 100 mL round-bottom flask and N-methylimidizole (NMI) (0.1 mL) was added with stirring. Diglycolic anhydride (0.45 g, 3.9 mmol) was added and the mixture was stirred overnight. The solvent was removed by rotary evaporation and the residue was dissolved in dichloromethane and washed with saturated $K_2HPO_4$ (aq) (4×). The organic layer was removed and dried over $MgSO_4$, filtered and the solvent was removed. The residue was vacuum dried to give 5 as a dark red, crisp foam. Yield 1.6 g, 80%.

1.5 Preparation of Conjugate Between Cyanine Dye Glycolate and 500 Å Controlled Pore Glass 6

Compound 5 (0.1 g, 0.1 mmol), Bop (0.05 g, 0.1 mmol), 1-hydroxybenzotriazole (HOBt) (0.02 g, 0.14 mmol) and acetonitrile (2 mL) were combined in a 20 mL scintillation vial. NMM (0.01 mL) was added and the mixture was stirred for 5 minutes. Aminopropylated 500 Å CPG (2.0 g) was added and the suspension was maintained overnight in a constant temperature water bath set to 30° C. The CPG was washed once with tetrahydrofuran (THF) using a sintered glass funnel. A capping solution was made by combining 10% acetic anhydride, 10% NMI and 10% pyridine in THF, and the CPG was contacted with this solution for 30 minutes. The CPG was washed repeatedly with THF, dichloromethane and finally with acetonitrile. The CPG ready for use after air drying overnight.

1.6 Preparation of 7 by conjugation of 1 with 2-(2-aminoethoxy)-ethanol

Compound 1 (2.5 g, 4.2 mmol) was combined with Bop (2.8 g, 6.3 mmol), NMM (1 mL) in dichloromethane (25 mL) and the mixture was stirred for 10 min. 2-(2-Aminoethoxy)-ethanol (0.67 g, 6.4 mmol) was added and the resulting mixture was stirred overnight. The organic layer was washed once with 0.5M hydrochloric acid (HCL), once with water and once with saturated sodium bicarbonate (aq). The organic layer was separated, dried over $MgSO_4$, filtered and the solvent was removed. The resulting residue was dried under high vacuum before purification. The crude product was submitted to column chromatography on a bed of alumina (4×20 cm), eluted with a gradient ranging from 0.5% pyridine: 99.5% dichloromethane to 2.5% MeOH: 0.5% pyridine: 97% dichloromethane. The fractions containing purified 7 were combined, the solvent was removed and the product vacuum dried overnight. Yield 1.9 g, 66%

1.7 Preparation of the Cyanine Dye Phosphoramidite 8 by Coupling 7 with Phosphane Phosphane (0.82 g, 2.7 mmol) and 1-H-tetrazole (0.051 g, 0.073 mmol) were dissolved in anhydrous MeCN (12 mL) and mixed for 1 min. Compound 7 (1.5 g, 2.2 mmol) was added, the components were mixed and allowed to sit for 2 h. The solvent was removed, the product dissolved in dichloromethane and washed once with dilute (2%) sodium hydrogen carbonate solution. The organic layer was separated, dried with $MgSO_4$, evaporated to dryness and vacuum dried to provide 8 as a dark red foam. Yield 1.5 g 79%

1.8 Preparation of an Oligonucleotide 9 Conjugated to Cyanine Dye 1

Compound 8 was dissolved in anhydrous MeCN at a concentration of 100 mg/mL and coupled to the 5' terminus of a mixed base 15-mer (3'-TTC-GAT-AAG-TCT-AGC-5') using the micro coupling protocol on a Biosearch 8700 Automated DNA Synthesizer.

1.9 Preparation of Phosphoramidite 10 from Serinol Cyanine Dye 4

Preparation of Oligonucleotide 11

Serinol cyanine dye 4 (1.9 g, 1.9 mmol) was azeotropically dried by co-evaporation with anhydrous MeCN. The azeotopically dried material was further dried under high vacuum overnight.

Phosphane (0.7 g, 2.3 mmol) was combined with 1-H-tetrazole (0.042 g, 0.06 mmol) in anhydrous MeCN (20 mL), stirred and let sit 1 min. Previously dried 4 (1.9 g, 1.9 mmol) was added, the resulting solution was mixed and allowed to sit for 2 h.

Serinol cyanine dye 15-mer oligonucleotide, 11, was prepared as described for 9.

1.10 Preparation of Conjugate 12, Formed Between 1 and N-Hydroxypiperidine

Compound 1 (2.5 g, 4.2 mmol), Bop (2.8 g, 6.3 mmol) and NMM (1 mL) were combined in dichloromethane (25 mL) and mixed for 10 min. 4-Hydroxypiperidine (0.64 g (6.3 mmol) was added and the resulting mixture was stirred overnight. The reaction mixture was washed once with 0.5M HCl, once with water and once with saturated sodium bicarbonate (aq). The organic layer was separated, dried over $MgSO_4$, filtered and the solvents were evaporated. The crude product was dried under high vacuum before purification. The crude product was purified by chromatography on alumina (4×20 cm) bed, eluted with a gradient ranging from 0.5% pyridine: 99.5% dichloromethane to 2.5% MeOH: 0.5% pyridine: 97% dichloromethane. Fractions containing the pure 12 were combined, the solvent was removed and the product was vacuum dried overnight.

1.11 Preparation of Phosphoramidite 13 by Coupling Cyanine Dye 12 with Phosphane Preparation of Oligonucleotide 14

Compound 12 (1.0 g, 1.5 mmol) was azeotropically dried by co-evaporation with anhydrous MeCN followed by maintaining under high vacuum overnight.

Phosphane (0.5 g, 1.7 mmol) and 1-H-tetrazole (0.03 g, 0.04 mmol) were dissolved in anhydrous MeCN (10 mL) and stirred for 10 min. Previously dried 11 (1.0 g, 1.5 mmol) was added and the mixture was allowed to sit for 2 h. The solvent was removed, the product dissolved in dichloromethane and washed once with dilute (2%) sodium hydrogen carbonate solution. The organic layer was separated and dried with $MgSO_4$. The solvent was removed and 13 was dried under high vacuum to dark red foam.

Cyanine dye 15-mer oligonucleotide, 14, was prepared as described for 9.

1.12 Preparation of Conjugate 15, Formed Between 1 and 6-Amino-1-Hexanol

Compound 1 (2.5 g, 4.2 mmol), Bop (2.8 g, 6.3 mmol) and NMM (1 mL) were combined with dichloromethane (25 mL) and mixed for 10 min. 6-amino-1-hexanol (0.75 g, 6.3 mmol) was added and mixed overnight. The reaction mixture was washed once with 0.5M HCl, once with water and once with saturated sodium bicarbonate (aq). The organic layer was dried over $MgSO_4$, filtered and the solvents were evaporated. The crude product was dried under high vacuum before purification. The crude product was chromatographed on alumina (4×20 cm), eluted with a gradient ranging from 0.5% pyridine: 99.5% dichloromethane to 2.5% MeOH: 0.5% pyridine: 97% dichloromethane. Fractions containing pure 15 were combined and evaporated to dryness and subsequently maintained under high vacuum.

1.13 Preparation of Phosphoramidite 16 by Coupling Cyanine Dye 15 with Phosphane Preparation of oligonucleotide 17

Compound 15 (1.0 g, 1.5 mmol) was azeotropically dried by co-evaporation with anhydrous MeCN and kept under high vacuum overnight.

Phosphane (0.5 g, 1.7 mmol) and 1-H-tetrazole (0.03 g, 0.04 mmol) were dissolved in anhydrous MeCN (10 mL)

and the mixture was stirred for 10 minutes. Previously dried 15 was added and the reaction mixture was allowed to sit for 2 h. The solvent was removed, the product dissolved in dichloromethane and washed once with dilute (2%) sodium hydrogen carbonate solution. The organic layer was separated, dried with MgSO$_4$, the solvent was removed and the residue was vacuum dried to dark red foam.

Cyanine dye 15-mer oligonucleotide, 17, was prepared as described for 9.

Example 2

2.1 Preparation of (1-(ε-carboxypentyl)-1'-(ethyl)-indo)-dicarbocyanine Dye 18

Compound 18 was prepared as described for compound 1, using N-hexanoic acid-2,3,3-trimethylindolinium (20 g, 72.89 mmol), malonaldehyde bis(phenylimine) (20 g 89.97 mmol) and N-ethyl-2,3,3-trimethylindolinium (20 g, 106.2 mmol). Yield: 31 g, 69%.

2.2 Preparation of 1-O-(4,4'-dimethoxytrityl)-2-amino-propan-3-ol conjugate 19 of 18

Compound 19 was prepared as described for 2, using compound 18 (3.5 g, 7.03 mmol), N-hydroxysuccinimide (0.9 g, 7.82 mmol), dichloromethane (100 mL) and dicyclohexylcarbodiimide (1.5 g, 7.27 mmol). Yield: 95%.

2.3 Preparation of Serinol Cyanine Dye 20 by Conjugation of 18 with 3

Compound 20 was prepared as described for 4, using 19 (6 g, 12.06 mmol), 3 (4.5 g 11.44 mmol) Bop (5.3 g 11.98 mmol) and 4-methylmorpholine (2 mL 18.19 mmol). Yield: 9.0 g, 75%.

2.4 Preparation of 21 by Reaction of 19 with Diglycolic Anhydride

Glycolate 21 was prepared as described for 5, using diglycolic anhydride (1.0 g, 8.62 mmol), 19 (4 g 4.58 mmol), dimethylethylamine (1 mL, 13.67 mmol) and dichloromethane (60 mL). Yield: 7.8 g, 79%.

2.5 Preparation of Conjugate Between Cyanine Dye Glycolate and 500 Å Controlled Pore Glass 22

The cyanine derivatized CPG was prepared as described for 6, using 21 (2.4 g 2.34 mmol), BOP (2 g, 4.52 mmol), HOBt (0.5 g, 3.7 mmol), NMM (1 mL, 9.1 mmol), aminopropyl CPG (50 g) and acetonitrile (80 mL).

2.6 Preparation of 21 by conjugation of 18 with 2-(2-aminoethoxy)-ethanol

Compound 21 was prepared as described for 7, using 18 (18 g, 36.17 mmol), Bop (20 g, 45.22 mmol), NMM (5 mL, 45.48 mmol), dichloromethane (200 mL) and 2-(2-aminoethoxy)-ethanol (5 g, 47.56 mmol). Yield: 14 g, 55%.

2.7 Preparation of the Cyanine Dye Phosphoramidite 22 by Coupling 6 with Phosphane Compound 22 was prepared as described for 7, using 15 g (21 mmol) of cyanine, 2-cyanoethyl-N,N,N',N'-tetraisopropyl phosphorodiamidite (8 g, 26.54 mmol), 1H-tetrazole (0.5 g, 7.14 mmol) and acetonitrile (100 mL). Yield: 15 g, 78%.

2.8 Preparation of the Serinol Cyanine Dye Phosphoramidite 23 from 20

Compound 23 was prepared as described for compound 10. The cyanine-labeled 15-mer oligonucleotide was prepared as described for 11.

The present invention provides a novel method of deprotecting and isolating oligonucleotides. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A method for detecting a nucleic acid target sequence, said method comprising:
   (a) contacting said target sequence with a detector oligonucleotide comprising a target binding sequence, said detector oligonucleotide having linked thereto,
     i) a cyanine dye, wherein said cyanine dye is covalently attached to said detector oligonucleotide by reaction of a reactive functional group on a cyanine dye reagent and a complementary group on said detector oligonucleotide, said cyanine dye reagent having the formula:

wherein
   $R^1$ is substituted or unsubstituted alkyl, or substituted or unsubstituted heteroalkyl groups and does not include a carboxylic acid ester moiety;
   $R^2$ is substituted or unsubstituted alkyl or substituted or unsubstituted heteroalkyl;
   $R^3$ is selected from the group consisting of H, substituted or unsubstituted alkyl, and substituted or unsubstituted heteroalkyl, or $R^2$ and $R^3$, together with the nitrogen to which they are attached, are optionally joined to form a substituted 5-7-membered heterocycloalkyl;

wherein one of $R^2$ and $R^3$ comprises said reactive functional group;

each of L is $C(R^{17})$ wherein each $R^{17}$ is selected from the group consisting of H, halide, substituted or unsubstituted alkyl and substituted or unsubstituted heteroalkyl, and wherein two adjacent $R^{17}$ groups may join to form a ring;

n is an integer selected from 1, 2, 3 and 4;

$R^4$, $R^5$, $R^6$, $R^7$, $R^8$, $R^9$, $R^{10}$, and $R^{11}$ are independently selected from the group consisting of substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN, $Z^1R^{19}$, $NR^{20}R^{21}$, and $C(Z^2)R^{22}$;

wherein two substituents selected from $R^4$, $R^5$, $R^6$ and $R^7$ on adjacent atoms of the 3H-indolium, together with the carbon atoms to which they are attached, are optionally joined to form an aromatic ring; and two substituents selected from $R^8$, $R^9$, $R^{10}$ and $R^{11}$ on adjacent atoms of the indoline, together with the carbon atoms to which they are attached, are optionally joined to form an aromatic ring;

$Z^1$ is O or S;

$Z^2$ is selected from the group consisting of O, S and NH;

$R^{19}$ and $R^{20}$ are independently selected from the group consisting of H, substituted or unsubstituted alkyl, and substituted or unsubstituted heteroalkyl;

$R^{21}$ is selected from the group consisting of H, substituted or unsubstituted alkyl and substituted or unsubstituted heteroalkyl and $C(Z^3)R^{22}$;

wherein $Z^3$ is selected from the group consisting of O, S and NH;

$R^{22}$ is selected from the group consisting of substituted or unsubstituted alkyl, substituted or unsubstituted heteroalkyl and $OR^{23}$, and $NR^{24}R^{25}$, wherein $R^{23}$ is selected from the group consisting of H, substituted or unsubstituted alkyl, substituted or unsubstituted heteroalkyl, substituted or unsubstituted aryl, substituted or unsubstituted heteroaryl and $C(O)R^{26}$ wherein $R^{26}$ is substituted or unsubstituted alkyl or substituted or unsubstituted heteroalkyl;

$R^{24}$ and $R^{25}$ are independently selected from the group consisting of H, substituted or unsubstituted alkyl and substituted or unsubstituted heteroalkyl;

or $R^{20}$ and $R^{21}$, together with the nitrogen to which they are attached, are selected from the group consisting of —$NHNH_2$, —N=C=S and —N=C=O;

$R^{12}$ is selected from the group consisting of substituted or unsubstituted alkyl, substituted or unsubstituted heteroalkyl, substituted or unsubstituted heterocycloalkyl, substituted or unsubstituted aryl and substituted or unsubstituted heteroaryl; and $R^{13}$, $R^{14}$, $R^{15}$ and $R^{16}$ are independently selected from the group consisting of H, substituted or unsubstituted alkyl and substituted or unsubstituted heteroalkyl; and ii) a quencher;

wherein said detector oligonucleotide is in a conformation allowing donor-acceptor energy transfer between said cyanine dye and said quencher when said cyanine dye is excited;

(b) hybridizing said target binding sequence to said target sequence, thereby altering said conformation of said detector oligonucleotide, causing a change in a fluorescence parameter; and (c) detecting said change in said fluorescence parameter, thereby detecting said nucleic acid target sequence.

2. The method according to claim 1, wherein said fluorescence parameter is detected in real time.

3. The method according to claim 1, wherein $R^2$ comprises said reactive functional group, and said reactive functional group is an oxygen-containing reactive functional group.

4. The method according to claim 3, wherein said oxygen-containing reactive functional group is selected from the group consisting of hydroxyl and phosphoramidite.

5. The method according to claim 1, wherein $R^1$ is unsubstituted alkyl;

$R^3$ is H;

$R^4$, $R^5$, $R^6$, $R^7$, $R^8$, $R^9$, $R^{10}$, and $R^{11}$ are each H;

$R^{12}$ is unsubstituted alkyl;

$R^{13}$, $R^{14}$, $R^{15}$ and $R^{16}$ are each unsubstituted alkyl; and $R^{17}$ is H.

6. The method according to claim 5, wherein n is 1 or 2.

7. The method according to claim 6, wherein $R^1$ is pentylene;

$R^{12}$ is ethyl; and $R^{13}$, $R^{14}$, $R^{15}$ and $R^{16}$ are each methyl.

8. The method according to claim 1, wherein the 3'-terminal nucleotide of said detector oligonucleotide is blocked or rendered incapable of extension by a nucleic acid polymerase.

9. The method according to claim 1, wherein said detector oligonucleotide is not required to adopt a secondary structure for said detector oligonucleotide to function.

10. The method according to claim 1, wherein two substituents selected from $R^4$, $R^5$, $R^6$ and $R^7$ on adjacent atoms of the 3H-indolium, together with the carbon atoms to which they are attached, are joined to form an aromatic ring; and two substituents selected from $R^8$, $R^9$, $R^{10}$ and $R^{11}$ on adjacent atoms of the indoline, together with the carbon atoms to which they are attached, are joined to form an aromatic ring.

11. The method according to claim 10, wherein said aromatic ring is phenyl.

12. The method according to claim 1, wherein one of $R^2$ and $R^3$ is attached to said detector oligonucleotide through a phosphodiester moiety.

13. A method for detecting amplification of a target sequence comprising, in an amplification reaction:

(a) hybridizing to said target sequence a detector oligonucleotide comprising a single-stranded target binding sequence and an intramolecularly associated secondary structure 5' to said target binding sequence, wherein at least a portion of said detector oligonucleotide is a single stranded tail which is available for hybridization to said target sequence, said detector oligonucleotide having linked thereto, i) a cyanine dye, wherein said cyanine dye is covalently attached to said detector oligonucleotide by reaction of a reactive functional group on a cyanine dye reagent and a complementary group on said detector oligonucleotide, said cyanine dye reagent having the formula:

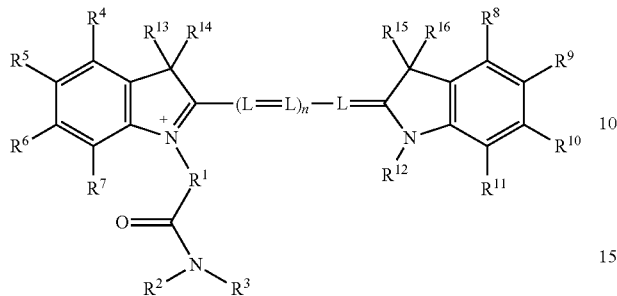

wherein
$R^1$ is substituted or unsubstituted alkyl or substituted or unsubstituted heteroalkyl groups and does not include a carboxylic acid ester moiety;
$R^2$ is substituted or unsubstituted alkyl or substituted or unsubstituted heteroalkyl;
$R^3$ is selected from the group consisting of H, substituted or unsubstituted alkyl, and substituted or unsubstituted heteroalkyl, or $R^2$ or $R^3$, together with the nitrogen to which they are attached, are optionally joined to form a substituted 5-7-membered heterocycloalkyl;
wherein one of $R^2$ and $R^3$ comprises said reactive functional group;
each of L is $C(R^{17})$
wherein each $R^{17}$ is a member independently selected from H, halide, substituted or unsubstituted alkyl and substituted or unsubstituted heteroalkyl, and wherein two adjacent $R^{17}$ groups may join to form a ring;
n is an integer selected from 1, 2, 3 and 4;
$R^4$, $R^5$, $R^6$, $R^7$, $R^8$, $R^9$, $R^{10}$, and $R^{11}$ are independently selected from the group consisting of substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN, $Z^1R^{19}$, $NR^{20}R^{21}$, and $C(Z^2)R^{22}$;
wherein
two substituents selected from $R^4$, $R^5$, $R^6$ and $R^7$ on adjacent atoms of the 3H-indolium, together with the carbon atoms to which they are attached, are optionally joined to form an aromatic ring; and
two substituents selected from $R^8$, $R^9$, $R^{10}$ and $R^{11}$ on adjacent atoms of the indoline, together with the carbon atoms to which they are attached, are optionally joined to form an aromatic ring;
$Z^1$ is a member selected from O and S;
$Z^2$ is a member selected from O, S and NH;
$R^{19}$ and $R^{20}$ are independently selected from the group consisting of H, substituted or unsubstituted alkyl, and substituted or unsubstituted heteroalkyl;
$R^{21}$ is selected from the group consisting of H, substituted or unsubstituted alkyl and substituted or unsubstituted heteroalkyl and $C(Z^3)R^{22}$;
wherein
$Z^3$ is selected from the group consisting of O, S and NH;
$R^{22}$ is selected from the group consisting of substituted or unsubstituted alkyl, substituted or unsubstituted heteroalkyl and $OR^{23}$, and $NR^{24}R^{25}$, wherein
$R^{23}$ is selected from the group consisting of H, substituted or unsubstituted alkyl, substituted or unsubstituted heteroalkyl, substituted or unsubstituted aryl, substituted or unsubstituted heteroaryl and $C(O)R^{26}$
wherein
$R^{26}$ is substituted or unsubstituted alkyl or substituted or unsubstituted heteroalkyl;
$R^{24}$ and $R^{25}$ are independently selected from the group consisting of H, substituted or unsubstituted alkyl and substituted or unsubstituted heteroalkyl;
or $R^{20}$ and $R^{21}$, together with the nitrogen to which they are attached, are selected from the group consisting of $-NHNH_2$, $-N=C=S$ and $-N=C=O$;
$R^{12}$ is selected from the group consisting of substituted or unsubstituted alkyl, substituted or unsubstituted heteroalkyl, substituted or unsubstituted heterocycloalkyl, substituted or unsubstituted aryl and substituted or unsubstituted heteroaryl; and
$R^{13}$, $R^{14}$, $R^{15}$ and $R^{16}$ are independently selected from the group consisting of H, substituted or unsubstituted alkyl and substituted or unsubstituted heteroalkyl; and
ii) a quencher,
wherein said detector oligonucleotide is in a conformation allowing donor-acceptor energy transfer between said cyanine dye and said quencher when said cyanine dye is excited;
(b) extending said hybridized detector oligonucleotide on said target sequence with a polymerase to produce a detector oligonucleotide extension product and separating said detector oligonucleotide extension product from said target sequence;
(c) hybridizing a primer to said detector oligonucleotide extension product and extending the primer with said polymerase, thereby linearizing said intramolecularly associated secondary structure and producing a change in a fluorescence parameter; and
(d) detecting said change in said fluorescence parameter, thereby detecting said target sequence.

14. The method according to claim 13, wherein said target sequence is amplified by a method selected from Strand Displacement Amplification, Polymerase Chain reaction, Self Sustained Sequence Replication, Transcription Mediated Amplification, and Nucleic Acid Sequence Based Amplification.

15. The method according to claim 13, wherein said secondary structure further comprises a partially or entirely single-stranded restriction endonuclease site.

16. The method according to claim 13, wherein a change in fluorescence intensity is detected.

17. The method according to claim 16, wherein said change in fluorescence intensity is detected in real-time.

18. The method according to claim 13, wherein said intramolecularly associated secondary structure comprises a portion of said target binding sequence.

19. The method according to claim 13, wherein $R^2$ comprises said reactive functional group, and said reactive functional group is an oxygen-containing reactive functional group.

20. The method according to claim 19, wherein said oxygen-containing reactive functional group is selected from the group consisting of hydroxyl and phosphoramidite.

21. The method according to claim 13,
wherein
$R^1$ is unsubstituted alkyl;
$R^3$ is H;

$R^4$, $R^5$, $R^6$, $R^7$, $R^8$, $R^9$, $R^{10}$, and $R^{11}$ are each H;
$R^{12}$ is unsubstituted alkyl;
$R^{13}$, $R^{14}$, $R^{15}$ and $R^{16}$ are each unsubstituted alkyl; and
$R^{17}$ is H.

22. The method according to claim 21, wherein n is 1 or 2.

23. The method according to claim 22,
wherein
$R^1$ is pentylene;
$R^{12}$ is ethyl; and
$R^{13}$, $R^{14}$, $R^{15}$ and $R^{16}$ are each methyl.

24. The method according to claim 13, wherein the 3'-terminal nucleotide of said detector oligonucleotide is blocked or rendered incapable of extension by a nucleic acid polymerase.

25. The method according to claim 13, wherein said detector oligonucleotide is not required to adopt a secondary structure for said detector oligonucleotide to function.

26. The method according to claim 13, wherein
two substituents selected from $R^4$, $R^5$, $R^6$ and $R^7$ on adjacent atoms of the 3H-indolium, together with the carbon atoms to which they are attached, are joined to form an aromatic ring; and
two substituents selected from $R^8$, $R^9$, $R^{10}$ and $R^{11}$ on adjacent atoms of the indoline, together with the carbon atoms to which they are attached, are joined to form an aromatic ring.

27. The method according to claim 26, wherein said aromatic ring is phenyl.

28. The method according to claim 13, wherein said intramolecularly associated secondary structure is selected from the group consisting of hairpins, stem-loop structures, pseudoknots, and triple helices.

29. The method according to claim 13, wherein one of $R^2$ and $R^3$ is attached to said detector oligonucleotide through a phosphodiester moiety.

30. A method for detecting a nucleic acid target sequence, said method comprising:
(a) contacting said target sequence with a detector oligonucleotide comprising a target binding sequence, said detector oligonucleotide having linked thereto,
i) a cyanine dye, wherein said cyanine dye is covalently attached to said detector oligonucleotide by reaction of a reactive functional group on a cyanine dye reagent and a complementary group on said detector oligonucleotide, said cyanine dye reagent having the formula:

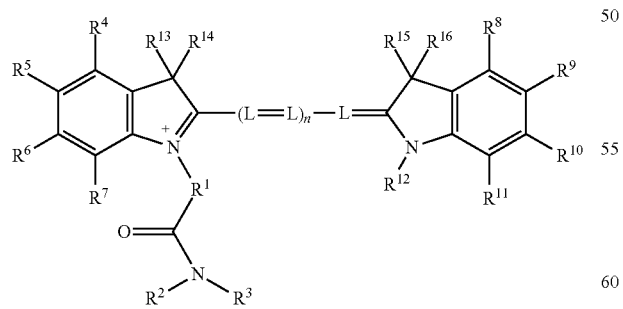

wherein
$R^1$ is a member selected from substituted or unsubstituted alkyl, and substituted or unsubstituted heteroalkyl groups and does not include a carboxylic acid ester moiety;

$R^2$ is a member selected from substituted or unsubstituted alkyl and substituted or unsubstituted heteroalkyl;
$R^3$ is selected from the group consisting of H, substituted or unsubstituted alkyl, and substituted or unsubstituted heteroalkyl, or $R^2$ and $R^3$, together with the nitrogen to which they are attached, are optionally joined to form a substituted 5-7-membered heterocycloalkyl;
wherein one of $R^2$ and $R^3$ comprises said reactive functional group;
-(L=L)$_n$-L= has a structure which is selected from the group consisting of:

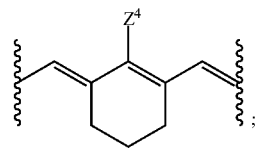

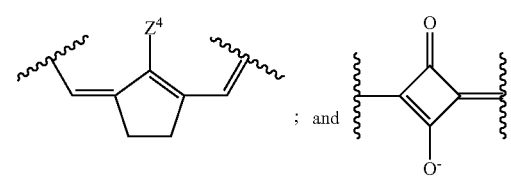

wherein
$Z^4$ is H, substituted or unsubstituted alkyl, substituted or unsubstituted heteroalkyl, substituted or unsubstituted aryl, substituted or unsubstituted heteroaryl, and substituted or unsubstituted heterocycloalkyl;
$R^4$, $R^5$, $R^6$, $R^7$, $R^8$, $R^9$, $R^{10}$, and $R^{11}$ are independently selected from the group consisting of substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, $NO_2$, CN, $Z^1R^{19}$, $NR^{20}R^{21}$, and $C(Z^2)R^{22}$;
wherein
$Z^1$ is a member selected from O and S;
$Z^2$ is selected from the group consisting of O, S and NH;
$R^{19}$ and $R^{20}$ are independently selected from the group consisting of H, substituted or unsubstituted alkyl, and substituted or unsubstituted heteroalkyl;
$R^{21}$ is selected from the group consisting of H, substituted or unsubstituted alkyl and substituted or unsubstituted heteroalkyl and $C(Z^3)R^{22}$;
wherein
$Z^3$ is selected from the group consisting of O, S and NH;
$R^{22}$ is selected from the group consisting of substituted or unsubstituted alkyl, substituted or unsubstituted heteroalkyl and $OR^{23}$, and $NR^{24}R^{25}$,
wherein
$R^{23}$ is selected from the group consisting of H, substituted or unsubstituted alkyl, substituted or unsubstituted heteroalkyl, substituted or unsubstituted aryl, substituted or unsubstituted heteroaryl and $C(O)R^{26}$ wherein
R²⁶ is substituted or unsubstituted alkyl or substituted or unsubstituted heteroalkyl;
R²⁴ and R²⁵ are independently selected from the group consisting of H, substituted or unsubstituted alkyl and substituted or unsubstituted heteroalkyl;
or R²⁰ and R²¹, together with the nitrogen to which they are attached, are selected from the group consisting of —NHNH₂, —N=C=S and —N=C=O;
R¹² is selected from the group consisting of substituted or unsubstituted alkyl, substituted or unsubstituted heteroalkyl, substituted or unsubstituted heterocycloalkyl, substituted or unsubstituted aryl and substituted or unsubstituted heteroaryl; and
R¹³, R¹⁴, R¹⁵ and R¹⁶ are independently selected from the group consisting of H, substituted or unsubstituted alkyl and substituted or unsubstituted heteroalkyl; and
ii) a quencher,
wherein said detector oligonucleotide is in a conformation allowing donor-acceptor energy transfer between said cyanine dye and said quencher when said cyanine dye is excited;
(b) hybridizing said target binding sequence to said target sequence, thereby altering said conformation of said detector oligonucleotide, causing a change in a fluorescence parameter; and
(c) detecting said change in said fluorescence parameter, thereby detecting said nucleic acid target sequence.

31. The method according to claim 30, wherein R² comprises said reactive functional group, and said reactive functional group is an oxygen-containing reactive functional group.

32. The method according to claim 31, wherein said oxygen-containing reactive functional group is selected from the group consisting of hydroxyl and phosphoramidite.

33. The method according to claim 30, wherein the 3'-terminal nucleotide of said detector oligonucleotide is blocked or rendered incapable of extension by a nucleic acid polymerase.

34. The method according to claim 30, wherein said detector oligonucleotide is not required to adopt a secondary structure for said detector oligonucleotide to function.

35. The method according to claim 30, wherein one of R² and R³ is attached to said detector oligonucleotide through a phosphodiester moiety.

36. A method for detecting amplification of a target sequence comprising, in an amplification reaction:
(a) hybridizing to said target sequence a detector oligonucleotide comprising a single-stranded target binding sequence and an intramolecularly associated secondary structure 5' to said target binding sequence,
wherein at least a portion of said detector oligonucleotide is a single stranded tail which is available for hybridization to said target sequence, said detector oligonucleotide having linked thereto,
i) a cyanine dye, wherein said cyanine dye is covalently attached to said detector oligonucleotide by reaction of a reactive functional group on a cyanine dye reagent and a complementary group on said detector oligonucleotide, said cyanine dye reagent having the formula:

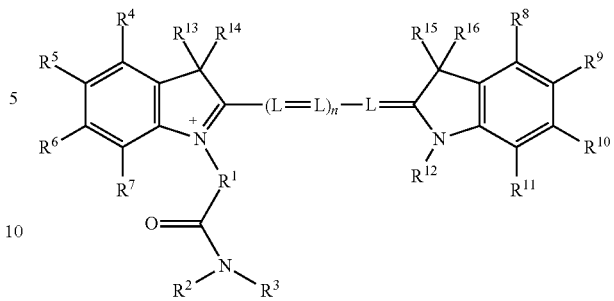

wherein
R¹ is a member selected from substituted or unsubstituted alkyl, and substituted or unsubstituted heteroalkyl groups and does not comprise a carboxylic acid ester moiety;
R² is a member selected from substituted or unsubstituted alkyl and substituted or unsubstituted heteroalkyl;
R³ is selected from the group consisting of H, substituted or unsubstituted alkyl, and substituted or unsubstituted heteroalkyl, or R² and R³, together with the nitrogen to which they are attached, are optionally joined to form a substituted 5-7-membered heterocycloalkyl;
wherein one of R² and R³ comprises said reactive functional group;
-(L=L)ₙ-L= has a structure which is a member selected from:

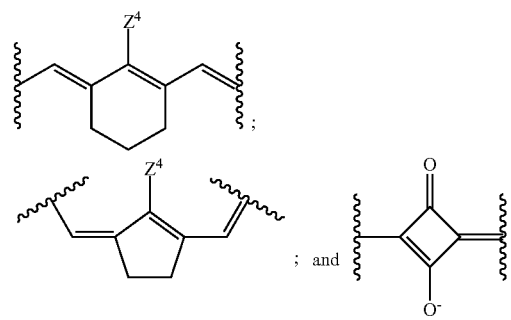

wherein
Z⁴ is H, substituted or unsubstituted alkyl, substituted or unsubstituted heteroalkyl, substituted or unsubstituted aryl, substituted or unsubstituted heteroaryl, and substituted or unsubstituted heterocycloalkyl;
R⁴, R⁵, R⁶, R⁷, R⁸, R⁹, R¹⁰, and R¹¹ are independently selected from the group consisting of substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, NO₂, CN, Z¹R¹⁹, NR²⁰R²¹, and C(Z²)R²²;
wherein
Z¹ is a member selected from O and S;
Z² is selected from the group consisting of O, S and NH;
R¹⁹ and R²⁰ are independently selected from the group consisting of H, substituted or unsubstituted alkyl, and substituted or unsubstituted heteroalkyl;
R²¹ is a member selected from H, substituted or unsubstituted alkyl and substituted or unsubstituted heteroalkyl and C(Z³)R²²;

wherein
Z³ is selected from the group consisting of O, S and NH;
R²² is selected from the group consisting of substituted or unsubstituted alkyl, substituted or unsubstituted heteroalkyl and OR²³, and NR²⁴R²⁵,
wherein
R²³ is selected from the group consisting of H, substituted or unsubstituted alkyl, substituted or unsubstituted heteroalkyl, substituted or unsubstituted aryl, substituted or unsubstituted heteroaryl and C(O)R²⁶
wherein
R²⁶ is substituted or unsubstituted alkyl or substituted or unsubstituted heteroalkyl;
R²⁴ and R²⁵ are independently selected from the group consisting of H, substituted or unsubstituted alkyl and substituted or unsubstituted heteroalkyl;
or R²⁰ and R²¹, together with the nitrogen to which they are attached, are selected from the group consisting of —NHNH₂, —N═C═S and —N═C═O;
R¹² is selected from the group consisting of substituted or unsubstituted alkyl, substituted or unsubstituted heteroalkyl, substituted or unsubstituted heterocycloalkyl, substituted or unsubstituted aryl and substituted or unsubstituted heteroaryl; and
R¹³, R¹⁴, R¹⁵ and R¹⁶ are independently selected from the group consisting of H, substituted or unsubstituted alkyl and substituted or unsubstituted heteroalkyl; and
ii) a quencher,
wherein said detector oligonucleotide is in a conformation allowing donor-acceptor energy transfer between said cyanine dye and said quencher when said cyanine dye is excited;
(b) extending said hybridized detector oligonucleotide on said target sequence with a polymerase to produce a detector oligonucleotide extension product and separating said detector oligonucleotide extension product from said target sequence;
(c) hybridizing a primer to said detector oligonucleotide extension product and extending the primer with said polymerase, thereby linearizing said intramolecularly associated secondary structure and producing a change in a fluorescence parameter; and
(d) detecting said change in said fluorescence parameter, thereby detecting said target sequence.

37. The method according to claim 36, wherein R² comprises said reactive functional group, and said reactive functional group is an oxygen-containing reactive functional group.

38. The method according to claim 37, wherein said oxygen-containing reactive functional group is selected from the group consisting of hydroxyl and phosphoramidite.

39. The method according to claim 36, wherein the 3'-terminal nucleotide of said detector oligonucleotide is blocked or rendered incapable of extension by a nucleic acid polymerase.

40. The method according to claim 36, wherein said detector oligonucleotide is not required to adopt a secondary structure for said detector oligonucleotide to function.

41. The method according to claim 36, wherein said intramolecularly associated secondary structure is selected from the group consisting of hairpins, stem-loop structures, pseudoknots, and triple helices.

42. The method according to claim 36, wherein one of R² and R³ is attached to said detector oligonucleotide through a phosphodiester moiety.

43. A method for detecting or quantifying a nucleic acid, said method comprising:
(a) contacting the nucleic acid with a mixture comprising at least a first carrier molecule and a second carrier molecule,
wherein
said first carrier molecule has covalently bound thereto a first quencher and a first fluorophore, wherein said first fluorophore is a cyanine dye, wherein said cyanine dye is covalently attached to said first carrier molecule by reaction of a reactive functional group on a cyanine dye reagent and a complementary group on said first carrier molecule, said cyanine dye reagent having the formula:

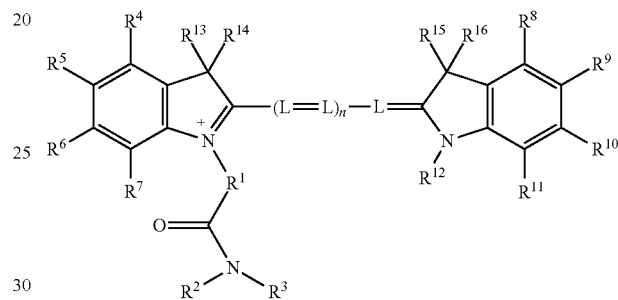

wherein
R¹ is a member selected from substituted or unsubstituted alkyl, and substituted or unsubstituted heteroalkyl groups and does not include a carboxylic acid ester moiety;
R² is a member selected from substituted or unsubstituted alkyl and substituted or unsubstituted heteroalkyl;
R³ is selected from the group consisting of H, substituted or unsubstituted alkyl, and substituted or unsubstituted heteroalkyl, or R² and R³, together with the nitrogen to which they are attached, are optionally joined to form a substituted 5-7-membered heterocycloalkyl;
wherein one of R² and R³ comprises said reactive functional group;
each of L is C(R¹⁷)
wherein each R¹⁷ is a member independently selected from H, halide, substituted or unsubstituted alkyl and substituted or unsubstituted heteroalkyl, and wherein two adjacent R¹⁷ groups may join to form a ring;
n is an integer selected from 1, 2, 3 and 4;
R⁴, R⁵, R⁶, R⁷, R⁸, R⁹, R¹⁰, and R¹¹ are independently selected from the group consisting of substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, NO₂, CN, Z¹R¹⁹, NR²⁰R²¹, and C(Z²)R²²;
wherein
two substituents selected from R⁴, R⁵, R⁶ and R⁷ on adjacent atoms of the 3H-indolium, together with the carbon atoms to which they are attached, are joined to form an aromatic ring; and
two substituents selected from R⁸, R⁹, R¹⁰ and R¹¹ on adjacent atoms of the indoline, together with the carbon atoms to which they are attached, are joined to form an aromatic ring $Z^1$ is a member selected from O and S;
$Z^2$ is selected from the group consisting of O, S and NH;
$R^{19}$ and $R^{20}$ are independently selected from the group consisting of H, substituted or unsubstituted alkyl, and substituted or unsubstituted heteroalkyl;
$R^{21}$ is selected from the group consisting of H, substituted or unsubstituted alkyl and substituted or unsubstituted heteroalkyl and $C(Z^3)R^{22}$;
wherein
$Z^3$ is selected from the group consisting of O, S and NH;
$R^{22}$ is selected from the group consisting of substituted or unsubstituted alkyl, substituted or unsubstituted heteroalkyl and $OR^{23}$, and $NR^{24}R^{25}$,
wherein
$R^{23}$ is selected from the group consisting of H, substituted or unsubstituted alkyl, substituted or unsubstituted heteroalkyl, substituted or unsubstituted aryl, substituted or unsubstituted heteroaryl and $C(O)R^{26}$
wherein
$R^{26}$ is a member selected from substituted or unsubstituted alkyl and substituted or unsubstituted heteroalkyl;
$R^{24}$ and $R^{25}$ are independently selected from the group consisting of H, substituted or unsubstituted alkyl and substituted or unsubstituted heteroalkyl;
or $R^{20}$ and $R^{21}$, together with the nitrogen to which they are attached, are selected from the group consisting of —NHNH$_2$, —N═C═S and —N═C═O;
$R^{12}$ is selected from the group consisting of substituted or unsubstituted alkyl, substituted or unsubstituted heteroalkyl, substituted or unsubstituted heterocycloalkyl, substituted or unsubstituted aryl and substituted or unsubstituted heteroaryl; and
$R^{13}$, $R^{14}$, $R^{15}$ and $R^{16}$ are independently selected from the group consisting of H, substituted or unsubstituted alkyl and substituted or unsubstituted heteroalkyl; and
said second carrier molecule has attached thereto a member selected from a second fluorophore, a second quencher and a combination thereof,
wherein said second fluorophore, said second quencher, or said second fluorophore and said second quencher is different from said first fluorophore and said first quencher, respectively; and
(b) detecting a change in a fluorescent property of one or more component of the mixture, the nucleic acid or a combination thereof, thereby detecting or quantifying the nucleic acid.

44. The method according to claim 43, wherein $R^2$ comprises said reactive functional group, and said reactive functional group is an oxygen-containing reactive functional group.

45. The method according to claim 44, wherein said oxygen-containing reactive functional group is selected from the group consisting of hydroxyl and phosphoramidite.

46. The method according to claim 43,
wherein
$R^1$ is unsubstituted alkyl;
$R^3$ is H;
$R^4$, $R^5$, $R^6$, $R^7$, $R^8$, $R^9$, $R^{10}$, and $R^{11}$ are each H;
$R^{12}$ is unsubstituted alkyl;
$R^{13}$, $R^{14}$, $R^{15}$ and $R^{16}$ are each unsubstituted alkyl; and
$R^{17}$ is H.

47. The method according to claim 46, wherein n is 1 or 2.

48. The method according to claim 47,
wherein
$R^1$ is pentylene;
$R^{12}$ is ethyl; and
$R^{13}$, $R^{14}$, $R^{15}$ and $R^{16}$ are each methyl.

49. The method according to claim 43, wherein said first carrier molecule is a nucleic acid probe, wherein the 3'-terminal nucleotide of said nucleic acid probe is blocked or rendered incapable of extension by a nucleic acid polymerase.

50. The method according to claim 43, wherein said first carrier molecule is a nucleic acid probe, wherein said nucleic acid probe does not require said first carrier molecule to adopt a secondary structure for said nucleic acid probe to function.

51. The method according to claim 43, wherein said aromatic ring is phenyl.

52. The method according to claim 43, wherein one of $R^2$ and $R^3$ is attached to said first carrier molecule through a phosphodiester moiety.

53. A method for detecting or quantifying a nucleic acid, said method comprising:
(a) contacting the nucleic acid with a mixture comprising at least a first carrier molecule and a second carrier molecule,
wherein
said first carrier molecule has covalently bound thereto a first quencher and a first fluorophore, wherein said first fluorophore is a cyanine dye, wherein said cyanine dye is covalently attached to said first carrier molecule by reaction of a reactive functional group on a cyanine dye reagent and a complementary group on said first carrier molecule, said cyanine dye reagent having the formula:

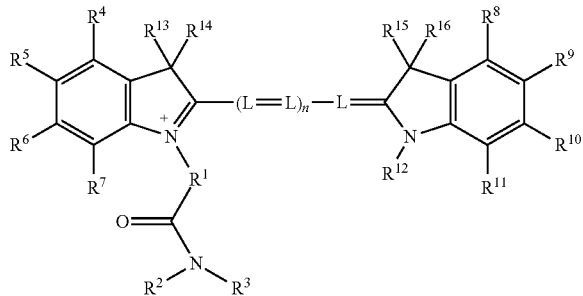

wherein
$R^1$ is a member selected from substituted or unsubstituted alkyl, and substituted or unsubstituted heteroalkyl groups and does not include a carboxylic acid ester moiety;
$R^2$ is a member selected from substituted or unsubstituted alkyl and substituted or unsubstituted heteroalkyl;
$R^3$ is selected from the group consisting of H, substituted or unsubstituted alkyl, and substituted or unsubstituted heteroalkyl, or $R^2$ and $R^3$, together with the nitrogen to which they are attached, are optionally joined to form a substituted 5-7-membered heterocycloalkyl;
wherein one of $R^2$ and $R^3$ comprises said reactive functional group;

-(L=L)$_n$-L= has a structure which is a member selected from:

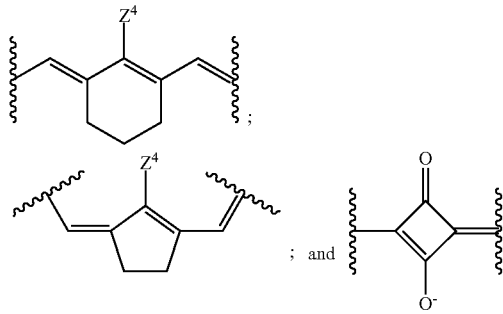

wherein
Z$^4$ is H, substituted or unsubstituted alkyl, substituted or unsubstituted heteroalkyl, substituted or unsubstituted aryl, substituted or unsubstituted heteroaryl, and substituted or unsubstituted heterocycloalkyl;

R$^4$, R$^5$, R$^6$, R$^7$, R$^8$, R$^9$, R$^{10}$, and R$^{11}$ are independently selected from the group consisting of substituted or unsubstituted alkyl, substituted or unsubstituted heteroalkyl, substituted or unsubstituted aryl, substituted or unsubstituted heteroaryl, substituted or unsubstituted heterocycloalkyl, halogen, H, NO$_2$, CN, Z$^1$R$^{19}$, NR$^{20}$R$^{21}$, and C(Z$^2$)R$^{22}$;

wherein
Z$^1$ is a member selected from O and S;
Z$^2$ is selected from the group consisting of O, S and NH;
R$^{19}$ and R$^{20}$ are independently selected from the group consisting of H, substituted or unsubstituted alkyl, and substituted or unsubstituted heteroalkyl;
R$^{21}$ is a member selected from H, substituted or unsubstituted alkyl and substituted or unsubstituted heteroalkyl and C(Z$^3$)R$^{22}$;

wherein
Z$^3$ is elected from the group consisting of O S and NH;
R$^{22}$ is selected from the group consisting of substituted or unsubstituted alkyl, substituted or unsubstituted heteroalkyl and OR$^{23}$, and NR$^{24}$R$^{25}$, wherein
R$^{23}$ is selected from the group consisting of H, substituted or unsubstituted alkyl, substituted or unsubstituted heteroalkyl, substituted or unsubstituted aryl, substituted or unsubstituted heteroaryl and C(O)R$^{26}$ wherein
R$^{26}$ is substituted or unsubstituted alkyl or substituted or unsubstituted heteroalkyl;
R$^{24}$ and R$^{25}$ are independently selected from the group consisting of H, substituted or unsubstituted alkyl and substituted or unsubstituted heteroalkyl;
or R$^{20}$ and R$^{21}$, together with the nitrogen to which they are attached, are selected from the group consisting of —NHNH$_2$, —N=C=S and —N=C=O;

R$^{12}$ is selected from the group consisting of substituted or unsubstituted alkyl, substituted or unsubstituted heteroalkyl, substituted or unsubstituted heterocycloalkyl, substituted or unsubstituted aryl and substituted or unsubstituted heteroaryl; and R$^{13}$, R$^{14}$, R$^{15}$ and R$^{16}$ are independently selected from the group consisting of H, substituted or unsubstituted alkyl and substituted or unsubstituted heteroalkyl;

said second carrier molecule has attached thereto a member selected from a second fluorophore, a second quencher and a combination thereof,
wherein said second fluorophore, said second quencher, or said second fluorophore and said second quencher is different from said first fluorophore and said first quencher, respectively; and (b) detecting a change in a fluorescent property of one or more component of the mixture, the nucleic acid or a combination thereof, thereby detecting or quantifying the nucleic acid.

54. The method according to claim 53, wherein R$^2$ comprises said reactive functional group, and said reactive functional group is an oxygen-containing reactive functional group.

55. The method according to claim 54, wherein said oxygen-containing reactive functional group is selected from the group consisting of hydroxyl and phosphoramidite.

56. The method according to claim 53, wherein said first carrier molecule is a nucleic acid probe, wherein the 3'-terminal nucleotide of said nucleic acid probe is blocked or rendered incapable of extension by a nucleic acid polymerase.

57. The method according to claim 53, wherein said first carrier molecule is a nucleic acid probe, wherein said nucleic acid probe does not require said first carrier molecule to adopt a secondary structure for said nucleic acid probe to function.

58. The method according to claim 53, wherein one of R$^2$ and R$^3$ is attached to said first carrier molecule through a phosphodiester moiety.

* * * * *